United States Patent [19]
Leader et al.

[11] Patent Number: 6,022,463
[45] Date of Patent: *Feb. 8, 2000

[54] SENSORS WITH SUBMINIATURE THROUGH HOLES

[75] Inventors: Matthew J. Leader, Laguna Niguel; Jeffrey Graves, San Clemente, both of Calif.

[73] Assignee: SenDx Medical, Inc., Carlsbad, Calif.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/649,009

[22] Filed: May 16, 1996

[51] Int. Cl.⁷ ........................ G01N 27/333; G01N 27/404
[52] U.S. Cl. .......................... 204/416; 204/403; 204/412; 204/415; 204/418; 204/419; 205/783; 205/787.5; 205/789.5
[58] Field of Search .................... 204/403, 415, 204/416, 418, 419, 412; 205/782.5, 783, 789, 789.5, 787.5

[56] References Cited

U.S. PATENT DOCUMENTS

| | | | |
|---|---|---|---|
| 3,740,326 | 6/1973 | Grubb | 204/418 |
| 3,833,495 | 9/1974 | Grubb | 204/435 |
| 3,997,420 | 12/1976 | Buzza | 204/420 |
| 4,214,968 | 7/1980 | Battaglia et al. | 204/418 |
| 4,225,410 | 9/1980 | Pace | 204/412 |
| 4,283,261 | 8/1981 | Maurer et al. | 204/408 |
| 4,454,007 | 6/1984 | Pace | 204/403 |
| 4,549,951 | 10/1985 | Knudson et al. | 204/418 |
| 4,565,665 | 1/1986 | Fogt | 204/418 |
| 4,758,325 | 7/1988 | Kanno et al. | 204/418 |
| 4,818,361 | 4/1989 | Burgess et al. | 204/406 |
| 4,871,439 | 10/1989 | Enzer et al. | 204/401 |
| 4,874,500 | 10/1989 | Madou et al. | 204/416 |
| 4,902,400 | 2/1990 | Usami | 204/408 |
| 4,948,473 | 8/1990 | Phillippi | 204/418 |
| 5,108,564 | 4/1992 | Szuminsky et al. | 204/412 |

(List continued on next page.)

FOREIGN PATENT DOCUMENTS

| | | |
|---|---|---|
| 0 653 629 A2 | 12/1990 | European Pat. Off. . |
| 0 532 440 A1 | 9/1992 | European Pat. Off. . |
| 0 607 748 A1 | 1/1993 | European Pat. Off. . |
| WO 93/13411 | 7/1993 | WIPO . |

*Primary Examiner*—T. Tung
*Attorney, Agent, or Firm*—Baker & Maxham

[57] ABSTRACT

The present invention is a sensor having an electrode formed in electrical contact with a subminiature through hole. Because of the small diameter of the through hole, the material that fills the through hole and the through hole itself have an essentially negligible effect on the sensor. A relatively large number of sensors can be formed on the surface of the substrate within a relatively small fluid flowcell. Thus, more information can be attained using less analyte. The sensors of the present invention are preferably disposed on an alumina substrate which is essentially impervious to aqueous electrolytes and blood over long periods of storage in potentially corrosive environments. Since the substrate on which the sensors are deposited, and the encapsulants which insulate the conductive elements of the sensor do not break down or become unstable when exposed over time to such corrosive environments, the isolation that is provided remains very high between each sensor and each other sensor, between each sensor and each conduction path, and between each conduction path and each other conduction path. The superior isolation provides for a high level of accuracy in the sensor of the present invention. Furthermore, the use of the through holes allows the conduction paths between the electrodes of the sensors and any external devices to be exclusively on the opposite side of the substrate from the sample. This physical isolation of the sample from the conduction paths between the sensor electrodes and external devices ensures very high electrical isolation between each of the sensors is maintained over an extended period time during which reactive fluids (such as electrolytes and/or blood) are present in the flowcell.

60 Claims, 11 Drawing Sheets

U.S. PATENT DOCUMENTS

| | | | |
|---|---|---|---|
| 5,246,576 | 9/1993 | Leader et al. | 204/415 |
| 5,271,820 | 12/1993 | Kinlen et al. | 204/418 |
| 5,310,469 | 5/1994 | Cunningham et al. | 204/403 |
| 5,336,388 | 8/1994 | Leader et al. | 204/418 |
| 5,338,435 | 8/1994 | Betts et al. | 204/408 |
| 5,385,846 | 1/1995 | Kuhn et al. | 204/403 |
| 5,458,646 | 10/1995 | Giachino et al. | 623/21 |
| 5,522,978 | 6/1996 | Pace | 204/418 |
| 5,547,555 | 8/1996 | Schwartz et al. | 204/415 |
| 5,607,566 | 3/1997 | Brown et al. | 204/418 |

SENSORS WITH SUBMINIATURE THROUGH HOLES

BACKGROUND OF THE INVENTION

1. Field of the Invention

This invention relates to systems for analyzing fluids and more particularly to an apparatus for determining partial pressures of blood gasses, concentrations of electrolytes, and hematocrit value of a fluid sample, and to a method for fabricating such an apparatus.

2. Description of Related Art

In a variety of instances it is desirable to measure the partial pressure of blood gasses in a whole blood sample, concentrations of electrolytes in the blood sample, and the hematocrit value of the blood sample. For example, measuring $pCO_2$, $pO_2$, pH, $Na^+$, $K^+$, $Ca^{2+}$ and hematocrit value are primary clinical indications in assessing the condition of a medical patient. A number of different devices currently exist for making such measurements. Such devices are preferably very accurate in order to provide the most meaningful diagnostic information. In addition, in an attempt to use as little of the patient's blood as possible in each analysis performed, the devices which are employed to analyze a blood sample are preferably relatively small. Performing blood analysis using a small blood sample is important when a relatively large number of samples must be taken in a relatively short amount of time or if the volume of blood is limited, as in neonates. For example, patients in intensive care require a sampling frequency of 15–20 per day for blood gas and clinical chemistry measurements, leading to a potentially large loss of blood during patient assessment. In addition, by reducing the size of the analyzer sufficiently to make the unit portable, analysis can be performed at the point of care. Also, reduced size typically means reduced turnaround time. Furthermore, in order to limit the number of tests which must be performed it is desirable to gather as much information as possible upon completion of each test. However, size limitations are imposed upon the sensors that are used to measure blood chemistry. These size limitations are in large part due to physical geometries of the sensors and the connections to the sensors. In a blood analyzer, disclosed in U.S. Pat. No. 4,818,361 a sensor assembly is fabricated in an attempt to reduce the size of the blood analyzer.

The sensor assembly has a plurality of sensors formed on a front side of a polymeric form along a flow path between an inlet and outlet port. The flow path is formed as a groove in a polymeric form. The form is either molded or machined. FIG. 1 illustrates a cross-sectional view of the sensor assembly. Electrodes are formed and communicate with a measurement flow channel 34 which is formed and which communicates with a measurement flow channel 34 which is established by the combination of form 30 and cover plate 32.

FIG. 1 illustrates a pH sensor 10 and a $CO_2$ sensor 20. Each sensor 10, 20 includes a wire 17 which is inserted through and substantially fills a hole 12 in the form 30. Upon inserting the wire 17 through the hole 12, it is critical to ensure that the wire 17 completely fills the hole 12. Gaps or cavities which form between the inner walls of the hole 12 and the wire 17 act as reservoirs in which contaminants which can contaminate the sensor electrode can be held. An adhesive is used to retain the wire 17 within the hole 12. Use of such adhesive further increases the risk that the electrode will be contaminated. The wire 17 may be friction fit within the hole 12. However, insertion of the wire 17 into a tight fitting hole is very difficult and requires excessive labor. Furthermore, even with the use of an adhesive, there is a risk that due to differences between the coefficient of expansion of the wire 17 and the form 30, the wire 17 will delaminate from the walls of the hole 12 under varying conditions of temperature and humidity.

It will be clear that such expansion and contraction can act as a pump, drawing traces of the analyte and/or other contaminates into the cavities between the wire 17 and the walls of the hole 12.

The end of the wire 17 opposite the measurement flow chamber 34 is coupled to electrical conductor 19 which serves as the electrical connection the to pH sensor 10. Conductor 19 may be in the form of a printed circuit conductor which lies upon the surface of form 30.

At the other end of electrode wire 17 is an electrochemically active layer 15. This electrochemically active layer 15 has essentially the same cross-sectional dimension as the wire 17 and serves to electrochemically couple wire 17 to an electrolyte layer 13. Another layer 11 is exposed to the fluid in the measurement channel 34 and covers the electrolyte layer 13. Accordingly, the shape and dimensions of the wire 17 dictate the dimensions of the electrochemically active layer of the sensor. Thus, the sensor dimensions are limited by the dimensions of wire stock which is available. In addition, the shape of the electro-chemically active layer of the sensor is limited by the shape of a cross-section of the wire 17 (i.e., essentially limiting the electro-chemically active layer of the sensor to a circular geometry). Still further, the use of wire 17 to fill the hole 17 places limitations on the thickness of the form, since insertion of the wire 17 into the hole 12 becomes difficult if the wire is short.

Furthermore, since the interface between the electrically active layer is relatively large, the wire must be of a material that is compatible with the electrically active layer to prevent negatively affecting the operation of the sensor. That is, over time, the conductive material of the wire contaminates the material used to form the electro-chemically active layer of the sensor, disrupting the electrochemical characteristics of the sensor. Therefore, constraints are placed on the material of the wires used to fill the holes 12. In one such assembly, the active layer 15 is formed from siver chloride, and the wire is formed from silver. The remaining portions of the pH sensor 10 are formed in a shallow well 14 which is concentric about the electrode hole 12. The inner layer 13 is an electrolyte layer. The $CO_2$ sensor 20 is similarly constructed.

In addition to the problems noted above, several other problems exist with this type of sensor. First, the process that is used to fabricate the assembly requires that each sensor assembly be handcrafted. Accordingly, fabrication of the sensor assembly requires a substantial amount of labor which is expensive and time consuming. The hole 12 associated with each sensor within the assembly must be filled with wire 12 by hand one sensor at a time. In addition to the amount of labor required to fill each sensor hole 12, variations in the quality of the operation and the conditions under which each hole 12 is filled increase the possibility that the entire assembly will operate below an acceptable performance standard due to one of the sensors exhibiting poor performance.

Second, the form 111 is fabricated from a polymeric material that tends to absorb some of the fluid which flows through the flow path 103. This absorbed fluid has a relatively low resistance compared with the very high resistance required between electrodes of the sensors 101. Accordingly, the initially high resistance which exists between the electrodes degrades. As the resistance between the conductive material 301 of each sensor degrades, the accuracy of the sensors 101 degrades as well.

Third, the electrical interface between the assembly and electronics external to the assembly is through an plurality of contacts which are fabricated on the rear surface of the form. These contacts slide against a spring loaded mating contact in the blood analyzer. As the contacts of the sensor assembly slide against the mating contacts within the blood analyzer, the contacts of the blood analyzer are worn down. Therefore, after being inserted and removed from the blood analyzer a number of times, the electrical connection between the external circuits within the blood analyzer and the sensors within the sensor assembly will be degraded.

In addition to these problems, the blood to be analyzed must be heated and regulated to a known stable temperature. Heating and stabilizing the temperature of the blood can take a substantial amount of time. Still further, in many cases analysis must be performed at regular and closely spaced intervals. Accordingly, if the heating and temperature stabilization time is relatively long, the number of times such analysis can be performed within a particular amount of time (i.e., turn around time) can be limited to a number less than would otherwise be desirable.

Accordingly, it would be desirable to provide sensors in a miniaturized panel configuration: (1) which remain accurate over a relatively long period of exposure to electrolytes and blood samples, (2) which uses a very small sample size, detects the concentration of a number of different electrolytes and the partial pressure of a number of blood gases all in a single analysis, and (3) in which a blood sample may be heated very rapidly to a known stable temperature.

SUMMARY OF THE INVENTION

The present invention is a sensor formed over a subminiature through hole. The sensor of the present invention may be (1) a potentiometric sensor, such as ion selective sensors; (2) an amperometric sensor (also known as polarographic sensor), such as an oxygen or sensor; or (3) a planar conductrimetric sensor, such as a hematocrit sensor. The subminiature through hole preferably has a diameter of approximately 0.002 to 0.006 inches. Because of the small diameter of the through hole, the material that fills the through hole and the through hole itself have an essentially negligible physical effect on the sensing electrode. For example, because each through hole has a small diameter, the overlying electrode will be essentially planar after filling the holes and depositing the layers of material which form the electrode. Also, only a small amount of conductive material which fills each through hole is in contact with each associated electrode. Therefore, the purity of the electrode is not significantly altered by the conductive material coupled to the electrode.

The through holes are laser drilled to a very accurate diameter. In accordance with the preferred embodiment of the present invention in which a 96% alumina substrate is used, after drilling, the substrate is annealed to remove any residue which attaches to the perimeter of the through holes. Annealing the substrate prevents contamination of the sensor electrodes which are to be deposited over the through holes.

The sensors of the present invention have very good signal-to-noise ratio due to the essentially impervious nature of the substrate when exposed to moisture, and due to the short electrical path length between the sensors and the external detecting and analyzing electronics within the blood analyzer. This short electrical path is a consequence of the use of the through holes to allow a more direct path between each sensor and the external electronics. Thus, unamplified, low level sensor outputs from the sensors can be used directly. The use of subminiature through holes to route electrical connections from the sensors to conductors on the back side of the substrate allows the sensors to be closely spaced on the surface of the substrate. Accordingly, a relatively large number of sensors can be formed on the surface of the substrate within a relatively small sample path. Thus, more information can be attained using less blood. Furthermore, since the substrate is relatively thin (0.025 inches) as well as small, the resulting smaller thermal mass of the sample permits the sample to be more rapid heated and the temperature more rapidly stabilized.

Furthermore, in accordance with the preferred embodiment of the present invention, a heater is disposed within the substrate. The heater is capable of heating a blood sample and the array of sensors to a known stable temperature and maintaining that temperature as the sample is being analyzed.

Still further, the sensors of the present invention are preferably disposed on an alumina substrate which is essentially impervious to aqueous electrolytes and blood over long periods of storage in potentially corrosive environments (such as in pouches in which the sensors are may be sealed to retain ambient conditions having relatively high humidity). In addition, each of the layers of thin film material used to fabricate the assembly of the present invention are unaffected by emersion into such corrosive environments. Since neither the substrate on which the sensors are deposited, nor any of the layers of material deposited thereon, will break down or become unstable when exposed over time to such corrosive environments, the isolation that is provided remains very high between each sensor and each other sensor, between each sensor and each conduction path, and between each conduction path and each other conduction path. The superior isolation provided by the substrate and subsequently deposited layers provides for a high level of accuracy in the sensor of the present invention. Furthermore, the use of the through holes allows the conduction paths between the electrodes of the sensors and any external devices to be exclusively on the opposite side of the substrate from the sample. This physical isolation of the sample from the conduction paths between the sensor electrodes and external devices ensures that very high electrical isolation between each of the sensors is maintained over an extended period time during which corrosive fluids (such as electrolytes and/or blood) are present in the flow-cell.

In addition, the sensors of the present invention can be fabricated in very small areas, allowing a relatively large number of sensors to be deposited in a small flowcell. Accordingly, the size of the flowcell, and thus the volume of the sample to be analyzed, can be significantly reduced. Reduction of the volume of the sample within the flowcell makes it possible to rapidly bring the sample and the sensors to a stable known temperature, thus reducing the amount of time required for analyzing the sample. Furthermore, because the sensors are relatively small, the number of sensors that can be used concurrently is increased. For example, in one embodiment of the present invention, sensors for $pCO_2$, $pO_2$, pH, $Na^+$, $K^+$, $Ca^{2+}$ and hematocrit value are all provided in a single relatively small sample chamber. In addition to the fact that the sensors of the present invention are relatively small, the use of a through hole disposed directly under each sensor, allows the entire wiring board of the present invention to be very compact. In the preferred embodiment of the present invention, the contact associated with each sensor on the non-sensor side of the substrate is in a geometric pattern which aligns the contact with a conventional surface mount electrical connector. The geometry of the sensors and the generally short conductors between the sensors and the connector result in short conduction paths to the signal processing electronics, and thus in a good signal-to-noise ratio undistored by electromagnetic radiation interference, in spite of the low signal level output from the electrodes.

BRIEF DESCRIPTION OF THE DRAWING

The objects, advantages, and features of this invention will become readily apparent in view of the following description, when read in conjunction with the accompanying drawings, in which.

Like reference numbers and designations in the various drawings refer to like elements.

DETAILED DESCRIPTION OF THE INVENTION

Throughout this description, the preferred embodiment and examples shown should be considered as exemplars, rather than limitations on the present invention.

Overview

Figure 1:
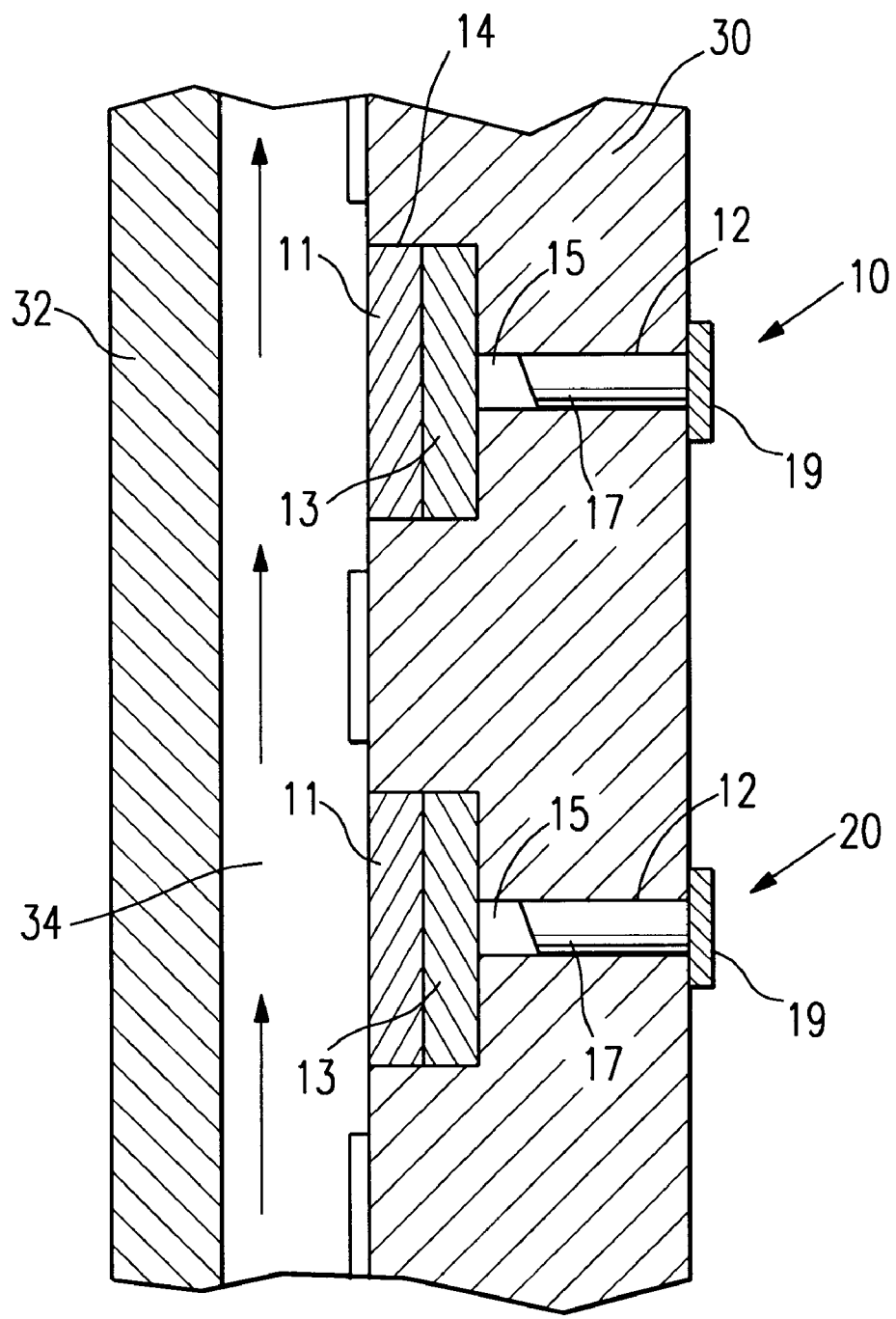
FIG. 1 is a cross-sectional view of a prior art sensor assembly.
Figure 2:
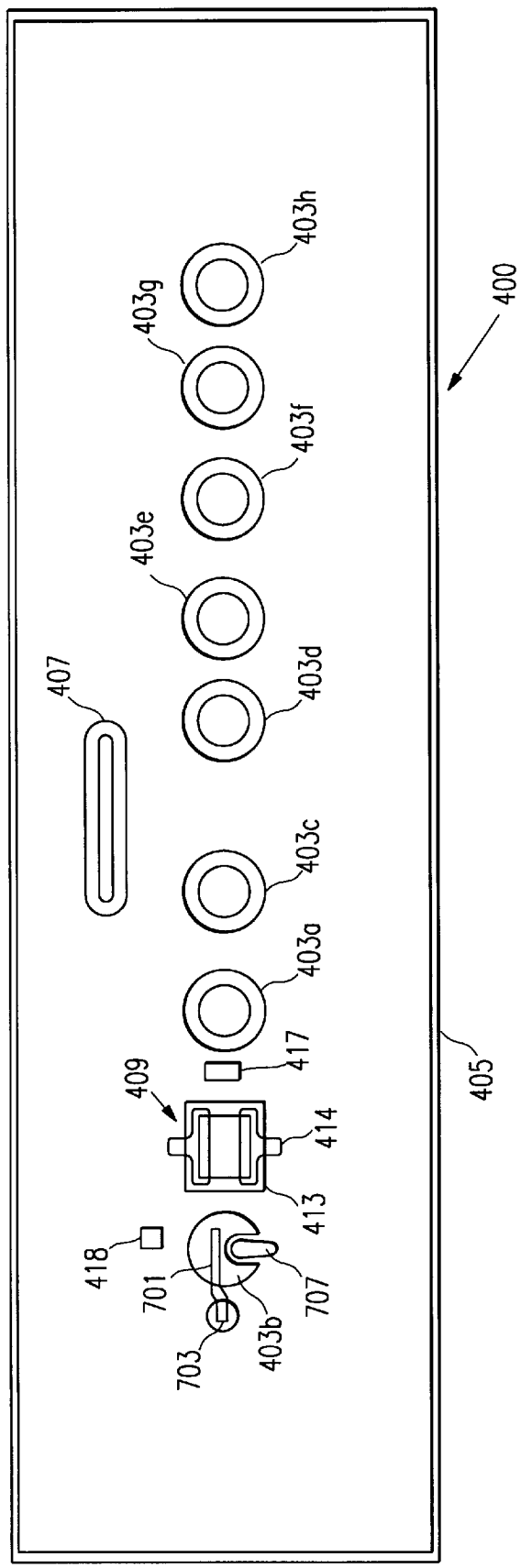
FIG. 2 is a front plan view of the sensor assembly of the present invention.
Figure 3:
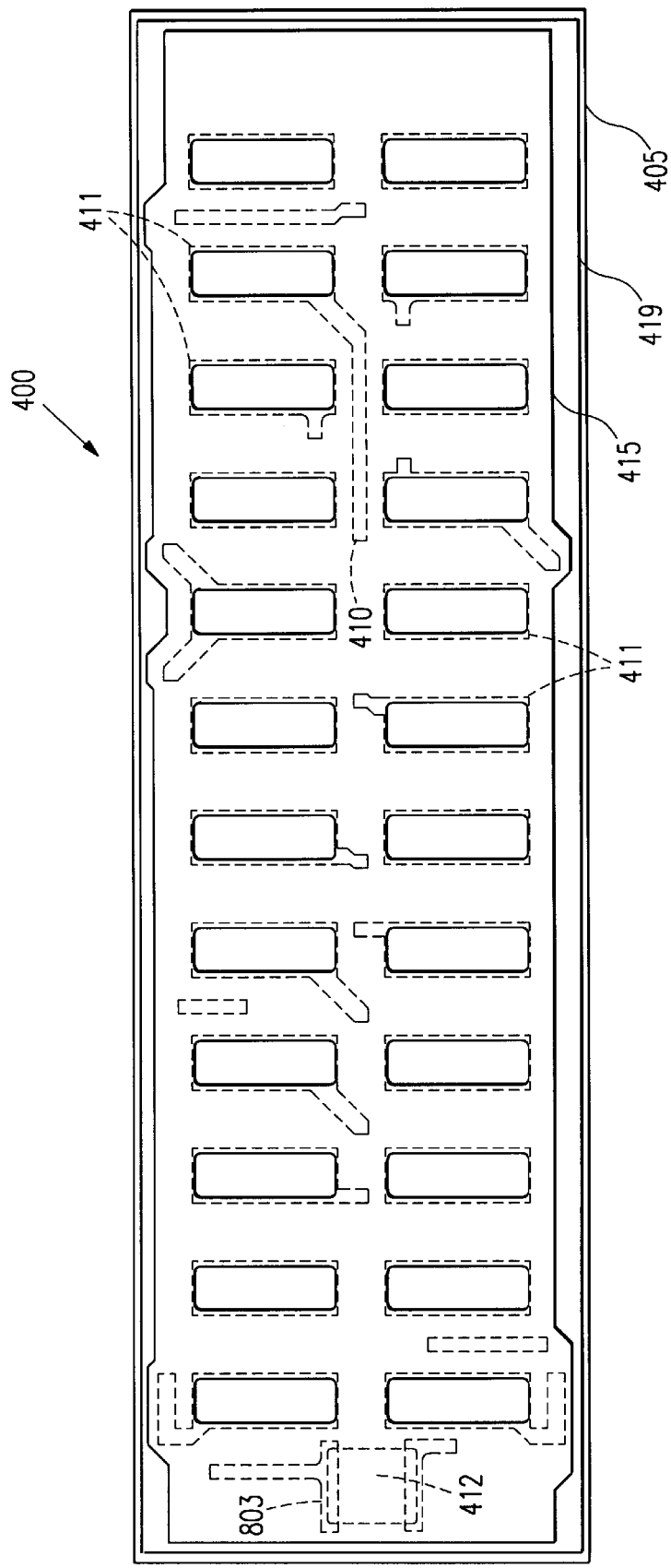
FIG. 3 is a back plan view of the sensor assembly of the present invention shown in FIG. 2.

FIG. 2 is a front plan view of one embodiment of the sensor assembly 400 of the present invention. FIG. 3 is a back plan view of the sensor assembly 400 of the present invention shown in FIG. 2. The present invention is a sensor assembly 400 having a plurality of sensors 403, including highly pure, planar circular silver potentiometric and amperometric electrode sensors disposed on an inorganic substrate 405. The sensor assembly 400 is preferably enclosed within a housing which defines a flowcell into which an analyte is transferred for analysis by the sensors 403. Each sensor 403 is preferably fabricated over a subminiature through hole through the substrate 405. In accordance with the preferred embodiment of the present invention, each subminiature through hole is preferably laser drilled through the substrate. These through holes reduce the amount of area required on the front side of the substrate by each of the sensors 403. That is, the present design geometry permits a number of sensors to be arrayed in a plane with fewer restrictions, since the layers of the conductors do not interfere with the placement of the sensor electrodes. Reducing the required area on the front side of the substrate allows a relatively large number of sensors 403 to be located in a relatively small area on the sensor assembly 400, and thus allows the volume of the flowcell to be reduced. Reducing the volume of the flowcell reduces the sample size, which is important, since in some situations many samples are required from the same patient. Furthermore, as a consequence of the small sample size, the low thermal mass of the sensor assembly 400, and the placement of a heater on the back side of the substrate, the present invention rapidly reaches a stable temperature at which analysis can be performed. Accordingly, the present invention can be installed into a blood analyzer (not shown) to provide rapid results (i.e., approximately 60 seconds in the case of one embodiment).

In addition to reducing the area required for each sensor 403, the use of subminiature through holes through the substrate under each sensor 403 allows the sample and reference solution to be physically isolated by the substrate 405 from the electrical conductors 410 which transfer electrical charge or current from each sensor electrode to an associated connector pad 411 (see FIG. 3). Only the sensor electrodes and a thermistor 409 are located on the front side of the substrate. The predominant use of the back side of the substrate to route conductors allows the front side of the substrate (i.e., where surface area is at a much greater premium) to be reserved for those elements which must reside on the front side (such as the sensor electrodes). It should be noted that the conductors 410 and pads 411 are shown using broken lines in FIG. 3 to illustrate that an encapsulant 415 is applied over the conductors 410 and a portion of the pads 411. As will be discussed in greater detail below, solder is deposited over the pads 411 to provide an appropriate electrical and physical interface to a surface mount connector (not shown in FIG. 3). As will also be described in more detail below, the thermistor 409 (see FIG. 2) is also encapsulated after being deposited on the front of the substrate 405. While the term "deposited" is used throughout this document, the meaning is intended to be inclusive of all means for forming a structure in a layered device, including screening, plating, thick film techniques, thin film techniques, pressurized laminating, photolithographic etching, etc.

In accordance with one embodiment of the present invention, all of the connections which couple the sensors 403 to external devices are deposited on the back side of the substrate. These connections are spaced apart to provide the greatest possible insulation resistance. In one embodiment of the present invention, electrical conductors are deposited on a plurality of different fabrication layers deposited on the back side of the substrate 405. No sample or reference solution contacts the back side of the substrate, as will be clear from the description provided below. A conventional surface mount electrical connector is preferably mounted on the connector pads to provide an electrical conduction path through a mechanical interface from the sensors 403 to external devices which detect and process the electrical signals generated by the sensors 403.

The substrate 405 of the preferred embodiment of the present invention is essentially impervious to aqueous electrolytes and blood over relatively long periods of time (i.e., more than six months in the case of one embodiment of the present invention). In accordance with the preferred embodiment of the present invention, the inorganic substrate 405 is a sheet of approximately 0.025 inch thick commercial grade 96% alumina ($Al_2O_3$). The substrate 405 is preferably stabilized by a heat treatment prior to purchase. One such substrate is available from Coors Ceramic Company, Grand Junction, Colo. Alternatively, the substrate may be any non-conductive essentially flat surface upon which the sensors may be deposited, as will be described in further detail below. For example, the substrate may be any silicon, glass, ceramic, wood product, non-conducting polymer or commercially available frit that can be used as a substantially smooth flat surface. However, the substrate preferably should be capable of withstanding the presence of an electrolyte having a pH of more than 6 to 9 and remaining essentially unaffected for an extended period of time (i.e., in the order of weeks).

Use of an alumina substrate provides the following advantages: (1) low thermal mass; (2) dimensional stability when subjected to aqueous electrolytes and blood for extended periods time; (3) establishes a mechanically and chemically stable substrate for use with thick film deposition techniques; (4) can be accurately laser drilled to high precision with very small diameter holes; (5) does not react with any of the materials which are used to fabricate sensors; and (6) very high electrical resistance. As a consequence of the fact that the assembly, including the inorganic substrate 405 and each deposited layer, is very stable and does not breakdown when subjected to aqueous electrolytes and blood, the sensor assembly 400 maintains very high isolation between (1) each of the sensors 403; (2) each of the sensors 403 and each electrical conductor; and (3) each of the electrical conductors.

Because the substrate 405 and each of the layers deposited thereon are stable and resists breakdown in the presence of aqueous electrolytes and blood, extremely high electrical resistance is maintained through the substrate. Accordingly, the present invention provides very high electrical isolation between each of the sensors 403, even after exposure to a reactive environment over a relatively long period of time. This is advantageous for the following reasons. In accordance with one embodiment of the present invention, an isotonic reference medium (e.g., a gel or other a viscous solution having a known ion concentration) is placed over a reference electrode to provide a reference for potentiometric sensors which are fabricated on the substrate 405. The present sensor assembly 400 can be stored in a sealed pouch (not shown) having a humidity that reduces evaporation of the isotonic reference medium. Storing the present invention in a sealed pouch having a controlled humidity also ensures that the sensors 403 remain partially hydrated during storage. Since the sensors 403 remain partially hydrated during storage of the sensor assembly 400, the sensors 403 of the present invention require minimal conditioning after installation. Therefore, having the sensors 403 stored in partially hydrated state greatly reduces the amount of time the user must wait before results can be attained from the sensors 403 of the present invention. This differs from prior art pH and $pCO_2$ sensors which are stored in an essentially dry environment. Such prior art sensors must be assembled or preconditioned many hours prior to use. It is advantageous to provide a sensor assembly 400 which is available for use shortly after installation. For example, blood laboratories which use prior art blood analyzers must maintain at least two such prior art blood analyzers or risk being out of service for many hours after replacement of a sensor assembly (i.e., the time required to assemble, condition, calibrate, and rehydrate the sensors). The sensor assembly of the present invention can output results in as little as 10 minutes from the time the sensor assembly is installed, thus reducing the need for a second blood analyzer which would otherwise be required as a backup.

In accordance with the sensor assembly 400 shown in FIGS. 2 and 3 the following sensors are provided: (1) sodium sensor 403h; (2) potassium sensor 403g; (3) calcium sensor 403f; (4) pH sensor 403e; (5) carbon dioxide sensor 403a; (6) oxygen sensor 403b; and (7) hematocrit value sensor 403c, 403d. A reference electrode 407 is also provided. The reference electrode is common to each of the potentiometric sensors (i.e., the sodium sensor 403h, potassium sensor 403g, calcium sensor 403f, pH sensor 403e, and carbon dioxide sensor 403a) and provides a voltage reference with respect to each such sensor. It will be understood by those skilled in the art that these sensors, or any subset of these sensors, may be provided in combination with other types of sensors.

Fabrication of the Sensor Assembly of the Present Invention

The following is the procedure by which one embodiment of the present invention is fabricated. It will be understood by those of ordinary skill in the art, that there are many alternative methods for fabricating the present invention. Accordingly, the description of the preferred method is merely provided as an exemplar of the present invention.

Initially, a series of through holes are drilled through the substrate 405. Preferably, each through hole is laser drilled using a $CO_2$ laser to a diameter in the range of approximately 0.002–0.006 inches, as measured on the front side of the substrate 405. By maintaining the small diameter of each through hole, the planar characteristic of an electrode which is deposited over the through hole is not distorted by the presence of the through holes. In the preferred embodiment of the present invention, thirteen holes are required, such that one hole is provided for each sensor, except for the hematocrit sensor 403c, 403d and the oxygen sensor 403b, each of which require two holes. The hematocrit sensor requires two holes in light of the two electrodes 403c, 403d. The oxygen sensor 403b preferably has one through hole for connection to the cathode of the sensor and one through hole for connection to the anode of the sensor. In addition, two through holes are preferably used for the connections to the thermistor 409. Also, two through holes are preferably used for the reference electrode 407 to reduce the risk of a defective through hole creating an open circuit. In the preferred embodiment of the present invention, each through hole that is associated with a sensor electrode is located under the location at which the associated sensor electrode to be deposited. Each such through hole is preferably located essentially at the center of the sensor electrode with the exception of the oxygen sensor 403*b*. However, in an alternative embodiment of the present invention, each through hole may be located anywhere underneath an electrode.

When the substrate 405 is a ceramic material, such as alumina, the substrate is preferably annealed after drilling all of the through holes at a temperature in the range of approximately 1000–1400° C., and more preferably in the range of approximately 1100–1200° C. Annealing the substrate after drilling ensures re-oxidation of a nonstoichiometric residue that attaches to the holes after the laser drilling. Without annealing, the residue (which is very reactive) contaminates the sensor electrodes, resulting in less pure electrode surfaces, which can lead to poor sensor performance. In the preferred embodiment of the present invention, the substrate is scribed after annealing. However, in an alternative embodiment of the present invention, the substrate may be scribed either before annealing, or not at all. Scribing the substrate allows several individual sensor assemblies formed in the same deposition processes on one substrate to be separated after all of the assemblies have been completed.

Once the through holes have been drilled and annealed, a thermistor paste is deposited in a predetermined pattern on the front side of the substrate 405 to form a thermistor 409 as shown in FIG. 2. In an alternative embodiment of the present invention, the particular geometry of the thermistor may vary from that shown in FIG. 2. In an alternative embodiment, the thermistor 409 is a discrete component which is not formed directly on the substrate. In the preferred embodiment of the present invention, the thermistor paste is part number ESL 2414, available from Electro-Science Laboratories, Inc. The thermistor paste 501 is preferably deposited to a thickness of approximately 15–29 $\mu$M when dried (10–22 $\mu$M when fired). The thermistor paste is oven dried and fired at a temperature of approximately 800–1000° C. for approximately 1–20 minutes. It will be understood by those skilled in the art that the thermistor 409 may be fabricated with any material that will provide information to an external control device by which the temperature of the sensor assembly 400 can be controlled. The thermistor is preferably be placed adjacent to any sensor that is particularly temperature sensitive or appropriately when measuring a temperature sensitive analyte. In an alternative embodiment of the present invention, a number of sensors and independently controllable heaters may be used to regulate the temperature of each sensor and the local temperature of the analyte at different locations along the flow path.

Once the thermistor paste has been deposited, dried, and fired, the substrate 405 is preferably placed in a vacuum fixture. The vacuum fixture (not shown) has a plurality of vacuum ports, each placed in contact with the opening of a through hole on the front side of the substrate. Preferably, each vacuum port is concurrently aligned with one of the through holes to create a relative low pressure within each through hole of the substrate with respect to the ambient pressure outside the through holes. A metallic paste, which is preferably compatible with the metal to be used to form the metallic layer of the electrodes of the electrolyte sensors 403*h*, 403*g*, 403*f*, as will be described in more detail below, is deposited over the through holes on the back side of the substrate 405. The deposited metal forms a conductive pad over the through hole. However, due to the vacuum applied to the front side of the substrate 405, a portion of the metal is drawn through the through holes. In accordance with the present invention, the metallic paste is preferably a silver paste, such as part number ESL 9912F, available from Electro-Science Laboratories, Inc. In accordance with the preferred embodiment of the present invention, the metallic paste is applied through a screen having a mesh density of 250 wires per inch (each wire having a diameter of approximately 0.0016 inches and a spacing of 0.0025 inches) and an emulsion thickness of approximately 0.0007 inches. The emulsion is developed to form a mask which allows the metal paste to pass through the screen only at the locations of the through holes on the back side of the substrate 405. The metallic paste is formed by the screen into columns above each through hole. Those columns of metal paste are then drawn down into the through holes by the reduction in pressure caused by the vacuum fixture. This procedure is preferably performed twice to ensure that each through hole is filled with the silver paste.

The substrate is then rotated to place the back side of the substrate 405 in contact with vacuum ports. The ports are aligned with the through holes over which the hematocrit electrodes 403*c*, 403*d* are to be deposited. The metal with which the front side of the through holes are filled is preferably selected to be compatible with the particular metal from which the electrode to be formed over the through hole is to be formed. In the preferred embodiment of the present invention, the hematocrit electrodes are formed using platinum. Therefore, the metallic material which fills the front side of these through holes and forms conductive pads on the front side of the substrate is preferably a silver/platinum paste, such as a mixture of silver paste, part number QS175, available from DuPont Electronics, and platinum paste, part number ESL 5545, available from Electro-Science Laboratories, Inc. The use of a silver/platinum paste presents a compatible interface between the platinum hematocrit sensor electrodes and the silver conductive material which fills the back side of the through holes which will underlie the hematocrit sensor electrodes. The mixture preferably has 50 parts silver, and 50 parts platinum. However, in an alternative embodiment, other alloys of silver and platinum may be used. Furthermore, any alloy which is compatible with platinum (i.e., with which platinum forms a solid solution), may be used. In a next screening process, each of the other eleven through holes (i.e., each of the through holes except the two over which the hematocrit electrodes 403*b*, 403*c* are to be deposited) are preferably filled from the front side of the substrate 405 using the same metallic paste that was previously used to fill the through holes from the back side of the substrate. Conductive pads, similar to the conductive pads formed on the back side of the substrate 405, are formed on the front side of the substrate 405. Filling the through holes from both the front and the back side of the substrate ensures that the entire through hole will be filled, and that a low resistance electrical contact will be made between the front and back side of the substrate through each through hole.

Figure 4:
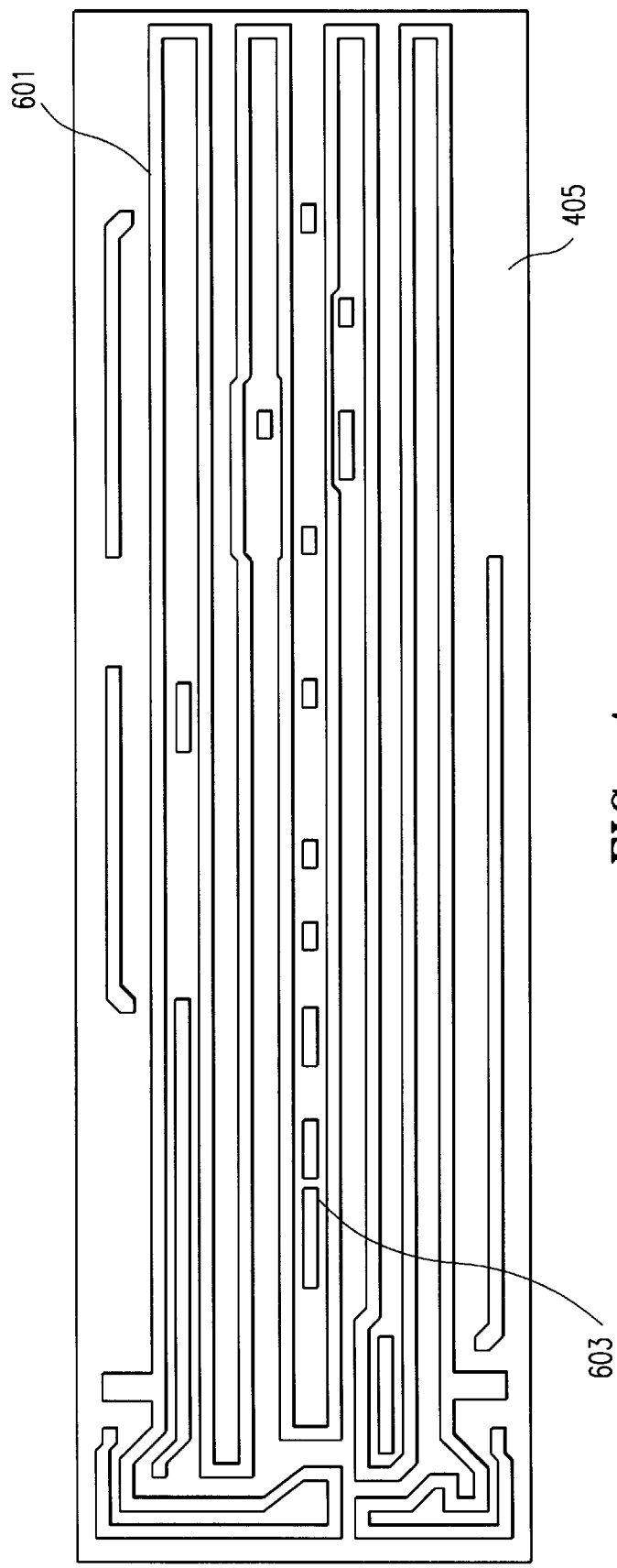
FIG. 4 is an illustration of one pattern to which a heater conforms when deposited on a substrate in accordance with the present invention.

FIG. 4 is an illustration of one pattern to which a heater 601 conforms when deposited on the substrate 405 in accordance with the present invention. In the embodiment shown, the heater 601 conforms generally to a complex serpentine pattern. FIG. 4 also shows a number of electrically conductive traces 603 which provide electrical conduction paths for current and/or electrical potential to be communicated from the electrodes of the sensors 403 to the pins of a connector to be affixed to the substrate, as will be described in greater detail below. The heater 601 is preferably deposited on the back side of the substrate 405. In accordance with one embodiment of the present invention, a heater paste blend including 10 parts of part number C4081, available from Heraeus Cermalloy, and 90 parts of part number 7484 available from DuPont Electronics is deposited to a thickness of 15–33 $\mu$M dried (7–20 $\mu$M fired). In accordance with one embodiment, a through hole vacuum may be applied to seal any through holes that remain open. It will be appreciated by those skilled in the art that the heater may be any heater device that provides a source of heat which can be readily controlled by a control device that receives information regarding temperature from the thermistor 409. It will also be appreciated that the particular routes taken by the conductors 603 may vary in alternative embodiments of the invention.

Figure 5:
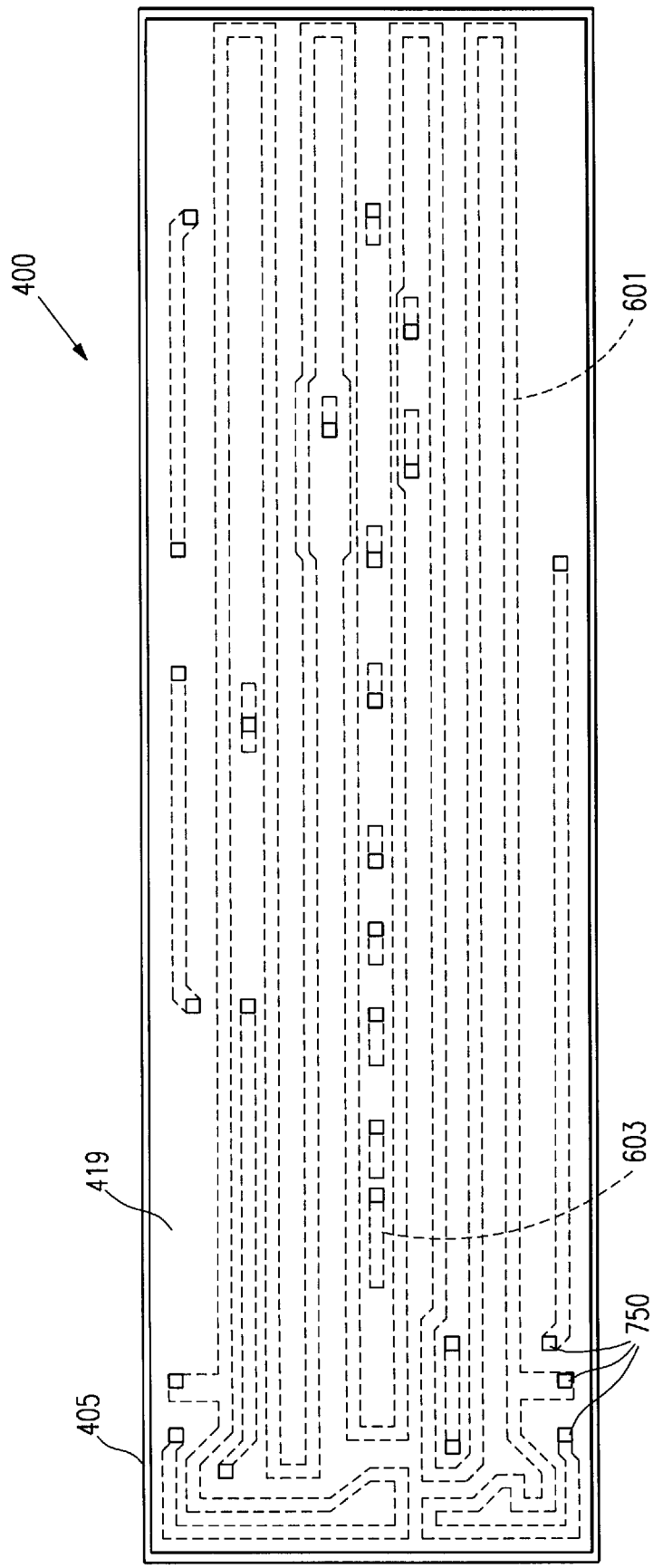
FIG. 5 is an illustration of the back side of a substrate after each of the dielectric layers have been deposited in accordance with one embodiment of the present invention.

Once the heater 601 and conductors 603 have been deposited, a series of dielectric layers 419 are deposited on the back side of the substrate 405 which electrically insulate the heater 601 and the conductors 603 from additional layers which are to be later deposited over the heater 601 and the conductors 603. The dielectric includes openings through which "vias" can be formed to provide electrical contact paths to the conductors 603 through the dielectric layers. A dielectric paste (such as part number 5704, available from E. I duPont) is applied to the back side of the substrate 405, preferably using a conventional thick film screening technique. The screen used to apply the dielectric paste masks all locations except those at which a via is to be formed. FIG. 5 is an illustration of the back side of the substrate 405 after each of the dielectric layers 419 have been deposited. It should be noted that the heater 601 and conductors 603 are shown in broken lines to indicate the presence of the dielectric layer 419 over the heater 601 and conductors 603. After two layers of the dielectric paste have been deposited, dried, and fired at a temperature of approximately 800°–950° C., a metallic paste, such as a palladium/silver composite, which in the preferred embodiment is part number 7484, available from E. I. DuPont, is deposited over those locations 750 at which vias are to be formed. In an alternative embodiment of the present invention, other noble metal mixtures can be used to achieve the desired resistance value within the available surface area. The metallic paste is then fired at 800°–950° C. for approximately 1 to 20 minutes. Two more layers of dielectric paste and metallic paste are deposited, each such layer being fired at 800°–950° C. for approximately 1 to 20 minutes directly after being deposited. It will be clear to those skilled in the art that other methods for depositing the dielectric layer and the vias may not require multiple layers of dielectric and metal. However, due to limitations on the thickness of layers which are deposited through a screen, more than one layer of both dielectric paste and metallic paste are preferably deposited. The dielectric layers between the conductive lines of the heater 601 build to a height which is nearly equal to the height of the dielectric layer over the heater 601, thus providing a relatively smooth surface at the back side of the sensor assembly 400.

Figure 6:
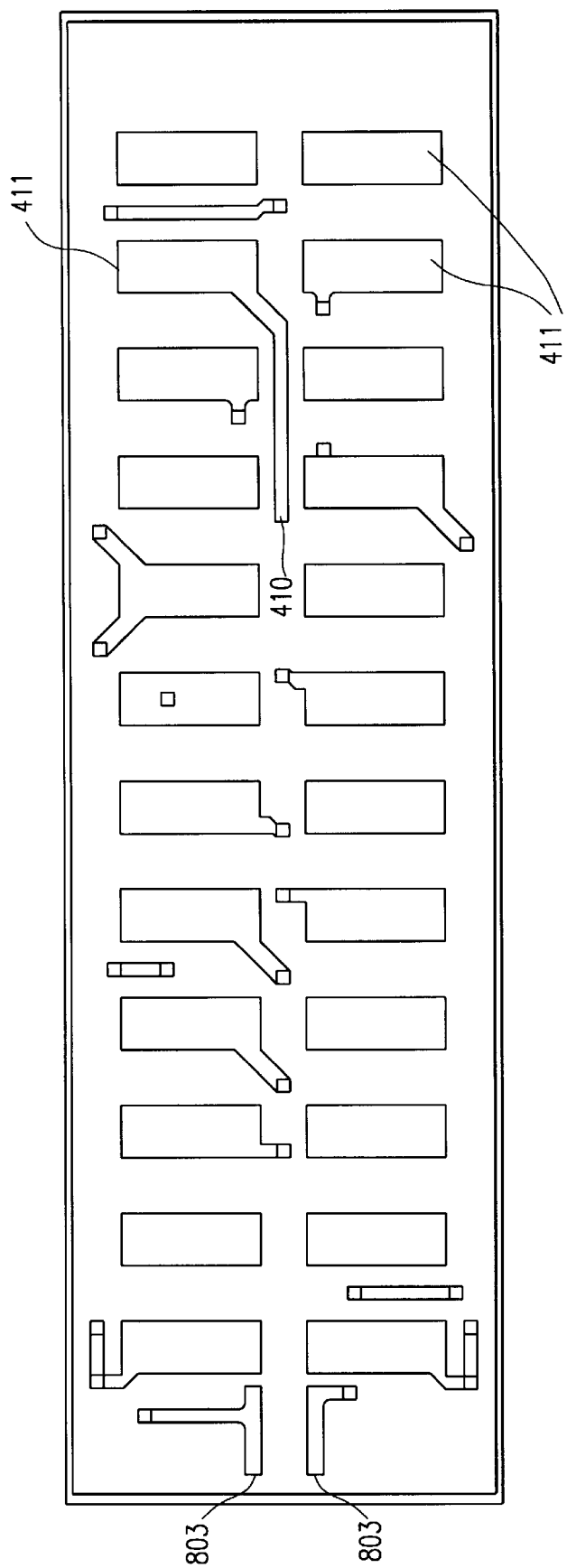
FIG. 6 is an illustration of the art work used to generate a screen, which in turn is used in the preferred embodiment of the present invention to deposit the second layer of conductors and connector pads.

After the last dielectric layer 419 is deposited, a second layer of conductors is deposited. FIG. 6 is an illustration of a second conductive layer, including the second layer of conductors 410, a plurality of connector pads 411, and connections 803 to the resistor 412 (see FIG. 3). In one embodiment of the present invention, the second conductive layer is formed from a metallic paste, such as palladium/silver, which in the preferred embodiment of the present invention is part number 7484 available from E. I duPont. The second conductive layer is then oven dried and fired at a temperature in the range of approximately 800°–950° C. for approximately 1 to 20 minutes. The conductors 410 and conductive connector pads 411 complete the connection between the sensor electrodes and external devices (not shown) coupled to the connector fixed to the connector pads 411. The second layer of conductors is oven dried and fired at a temperature in the range of approximately 800°–950° C. for approximately 1 to 20 minutes.

In accordance with the present invention, conductors 603, 410 are deposited on only two layers (i.e., the heater layer and the connector pad layer). However, in an alternative embodiment of the present invention in which the geometry of the sensor assembly 400 makes it difficult to route the conductors from each sensor to an appropriate electrical contact pad to which a connector is to be electrically coupled, more than two layers having conductors may be used. In such an embodiment, each such conductor layer is preferably separated by at least one layer of insulating dielectric material.

Figure 7:
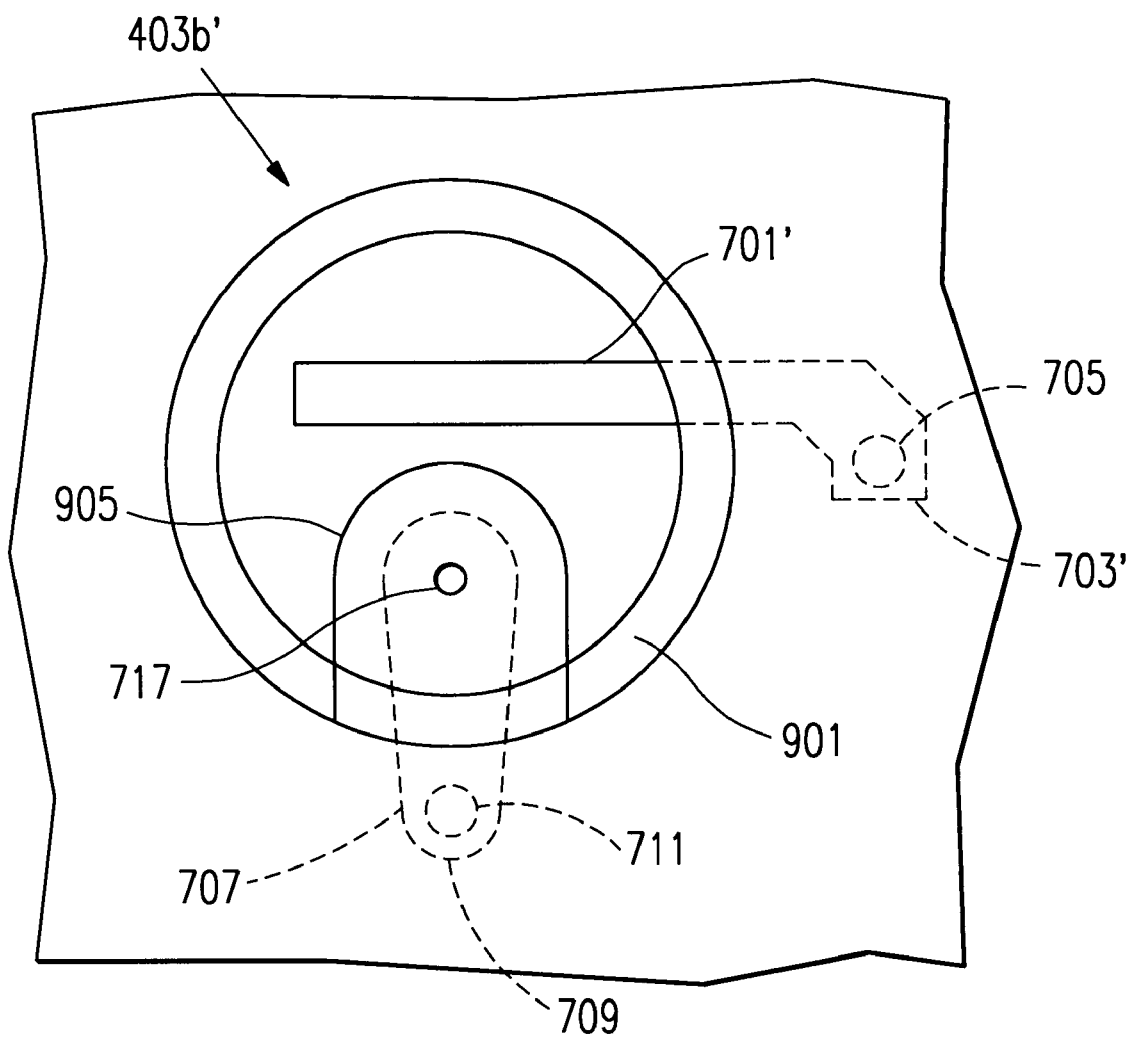
FIG. 7 is an illustration of an oxygen sensor in accordance with the preferred embodiment of the present invention.

After the second layer of conductors has been deposited on the back side of the substrate 405, each of the layers which form the electrodes of the sensors 403 are deposited on the front side of the substrate 405. Concurrent with the deposition of the first metal layer of each electrode, contacts 414 to the thermistor 409 are deposited to couple the thermistor to the through holes that are adjacent the thermistor 409 (see FIG. 2). FIG. 7 is an illustration of an oxygen sensor 403*b*' in accordance with an alternative embodiment of the present invention. Both the oxygen sensor 403*b* and 403*b*' are essentially conventional amperometric cells. The only difference between the oxygen sensor 403*b* shown in FIG. 2 and the oxygen sensor 403*b*' shown in FIG. 7 is the shape of the anodes 701, 701'. In accordance with the preferred embodiment of the present invention, the anodes 701, 701' are essentially straight conductors which deflect from straight at the distal end 703, 703'. Preferably, the area of the anode is a minimum of 50 times greater than the area of the cathode to ensure the most stable operation. In addition, the distance between the anode and the cathode is preferably approximately 0.020–0.030 inches to ensure that the potential developed across the anode to cathode is not too great. It should be noted that the anode of the oxygen sensor may be configured to conform to any number of alternative shapes. These two shapes are provided merely as exemplars of the shape of the anode in accordance with two particular embodiments of the present invention. In one embodiment of the present invention, a metal, such as silver paste, part number QS 175, available from DuPont Electronics, is deposited to form the anode 701, 701' of the oxygen sensor 403*b*'. Alteratively, any metal suitable for use in forming the anode of an amperometric cell may be used, such as platinum, ruthenium, palladium, rhodium, iridium, gold, or silver. A distal end 703, 703' of the anode 701, 701' is deposited over one of the above described through holes 705 through the substrate 403.

The cathode conductor 707 is then deposited. A distal end 709 of the cathode conductor 707 is deposited over another of the through holes 711 through the substrate 403. The cathode conductor 707 and the anode 701, 701' are oven dried and fired at a temperature of approximately 800° C. to 950° C. for approximately 1 to 20 minutes.

Figure 8:
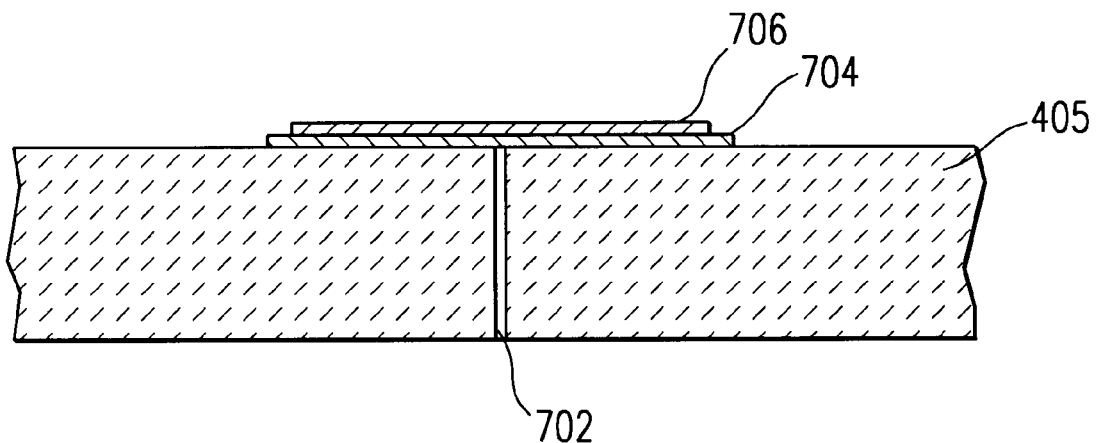
FIG. 8 is a cross-sectional view of a portion of a substrate through which a sensor through hole is formed and on which metal layers of an electrolyte sensor electrode have been deposited in accordance with one embodiment of the present invention.

FIG. 8 is a cross-sectional view of a portion of the substrate 405 through which a sensor through hole 702 is formed and on which metal layers of an ion sensitive sensor electrode have been deposited. Concurrent with the deposition of the oxygen sensor 403*b*, and by deposition of the same type of material (preferably silver) deposited to form the metallic layer of the anode 701, 701' of the oxygen sensor 403*b*, a first metallic layer 704 of each of the electrodes associated with each of the other sensors 403*a*, 403e–403h and the reference electrode 407 are deposited on the substrate over a through hole 702. In the case of sensors 403a, 403e–403h which are to have a polymeric membrane disposed over the metallic layer, a second metallic layer 706, preferably of the same material as the first metallic layer 704, is deposited over the first metallic layer 704 in order to reduce any distortion in the flatness of the surface due to the presence of the through hole 702 located beneath the first metallic layer 704. That is, electrodes formed over a through hole 702 with only one layer of metallic material tend to develop a depression over the through hole 702. Such a depression is generally of no consequence if the electrode is not to be coated with a polymeric membrane.

However, in sensors which have polymeric membranes, such a depression can cause the membrane to become embedded in the electrode 704. As a result of this distortion, optimal performance would not be achieved. That is, very uniform membrane geometry is important to achieving optimal sensor function and performance. This can be understood in light of the fact that in the preferred embodiment of the present invention, the thickness of a polymeric membrane that is applied over the metallic layers 704, 706 is determined by pouring a controlled volumetric quantity of a membrane solution into a sensor cavity having well defined dimensions (as will be discussed further below). The membrane formed over the metallic layer 706 is very thin (i.e., approximately 5–250 $\mu$M). Any variation in the thickness of the membrane at one point, effects the thickness of the membrane at each other point. Such variations in the thickness of the membrane adversely effect the performance of the sensor 403. Therefore, if a depression exists in the metallic layer which underlies the polymeric membrane, the membrane will be thicker over the depression, and thus thinner over the remainder of the electrode. Depositing a second metallic layer 706 smooths any such depression which might otherwise exist. The second metallic layer 706 preferably has a different diameter than the first layer 704 in order to reduce the chances that the metallic layers will puncture the polymeric membrane due to the abrupt edge that would be formed at the perimeter if both the first and second metallic layers 704, 706 were to have the same diameter. Since the presence of a depression is insignificant in electrodes of sensors which do not require a thin membrane, these sensors are preferably formed having only one metallic layer 704.

The preferred dimensions for the metallic layers 704, 706 of each sensor in accordance with one embodiment of the present invention are provided below. It will be understood by those skilled in the art that other dimensions may be quite suitable for fabricating sensors. However, the dimensions presented reflect a tradeoff between reduced impedance and reduced size. A tradeoff is required because of the desire to form the sensor in as small an area as possible, and the competing desire to form a sensor which has a relatively low impedance. These two goals are incompatible because of the inverse relationship between size and impedance. That is, in general, size is inversely proportional to impedance. Therefore, the greater the size of the sensor electrode, the smaller the impedance of that electrode.

The diameter of the first metallic layer 704 of the $CO_2$ sensor 403a, the pH sensor 403e, and each of the electrolyte sensors 403f, 403g, 403h is 0.054 inches. The diameter of the second electrode layer 706 of each of these sensors is 0.046 inches. The second layer 706 is deposited over the first layer 704. The metallic layer 704 of the reference electrode is generally rectangular, having rounded corners with radius equal to one half the width of the electrode. The width of the electrode is preferably 0.01 inches, and the length is preferably 0.08 inches. It will be understood by those skilled in the art that the reference electrode 407 may be formed in numerous other shapes. After the first metallic layer 704 is deposited, the substrate 405 is oven dried and fired at approximately 800°–950° C. for approximately 1–20 minutes. After deposition, the second metallic layer 706 is similarly dried and fired. Each of the metallic layers 704, 706 is preferably 16–36 $\mu$M thick after drying, and 7–25 $\mu$M thick after firing.

Figure 9:
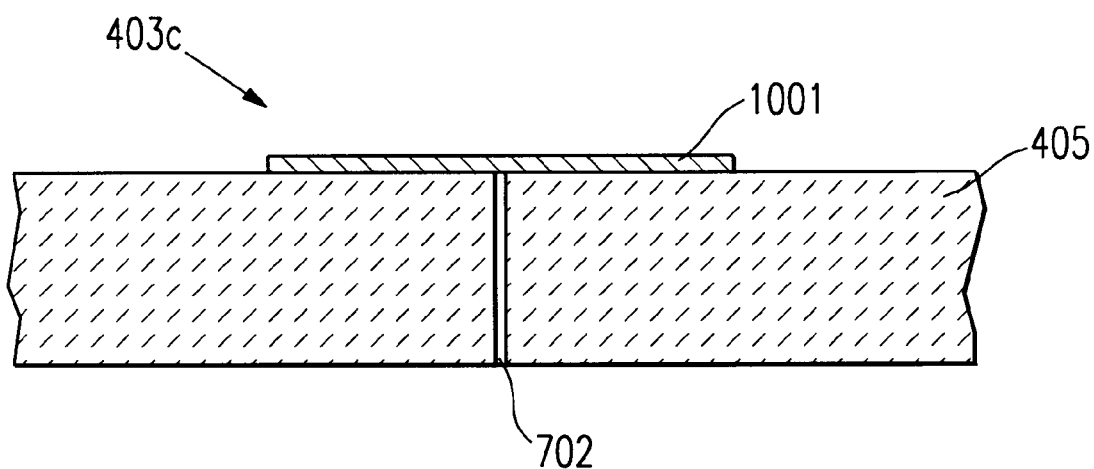
FIG. 9 is a cross-sectional view of one of the hematocrit sensor electrodes in accordance with one embodiment of the present invention.

FIG. 9 is a cross-sectional view of one of the hematocrit sensor electrodes 403c. Only one of the two electrodes 403c, 403d are shown, since each are essentially identical. In accordance with the preferred embodiment of the present invention, the metal used to form the electrodes of the hematocrit sensor 403c, 403d differs from the metal 704, 706 used to form the electrodes of the electrolyte sensors 403f, 403g, 403h, the pH sensor 403e, the oxygen sensor 403a, and the reference electrode 407. Therefore, in the preferred embodiment, the electrodes of the hematocrit sensor 403c, 403d are formed by depositing a third metallic layer 1001. Since no polymeric membrane is to be placed over the metallic layer 1001 of the hematocrit electrodes 403c, 403d, the hematocrit electrodes 403c, 403d preferably only have one metallic layer. In the preferred embodiment of the present invention, the metal used to form the electrodes for the hematocrit sensor 403c, 403d is a cermet platinum conductor, such as part number ESL 5545, available from Electro-Science Laboratories, Inc. The diameter of the metallic layer 1001 of each hematocrit sensor electrode is 0.054 inches. The hematocrit sensor electrodes 403c, 403d are preferably spaced approximately 0.15 inches apart.

After forming the metallic layer 1001 of the hematocrit sensor electrodes 403c, 403d, the cathode conductor 707 (see FIG. 7) is deposited. In accordance with the preferred embodiment of the present invention, the cathode conductor 707 is formed from a gold paste, such as part number ESL 8880H, available from Electro-Science Laboratories, Inc. It will be understood by those skilled in the art that the cathode conductor 707 may be fabricated from any metal commonly used to form a cathode of a conventional amperometric cell. However, it should be noted that the level of contaminants in the paste will effect the sensor characteristics. Furthermore, in an alternative embodiment of the present invention, the particular geometry of the cathode conductor 707 may vary from that shown in FIG. 7. At the same time that the cathode conductor 707 is deposited, a pair of laser targets 417, 418 are preferably deposited. The laser targets 417, 418 provide a reference which is used to form a cathode 717, as will be discussed in greater detail below. Once deposited, the cathode conductor 707 is dried and fired at a temperature of 800°–950° C. for approximately 1 to 20 minutes.

Figure 10:
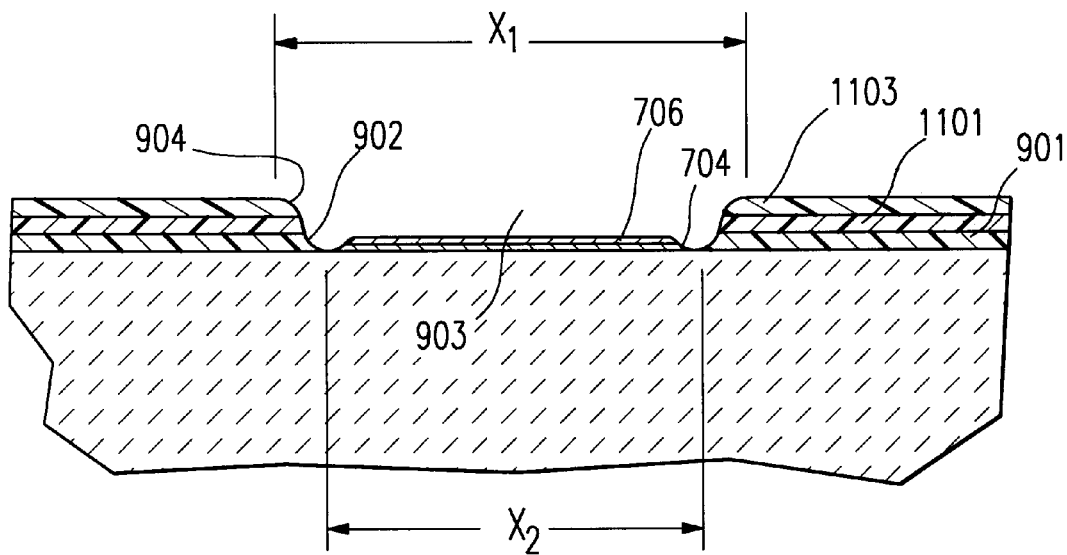
FIG. 10 is a cross-sectional view of a sensor showing the first layer of encapsulant in accordance with one embodiment of the present invention.
Figure 11:
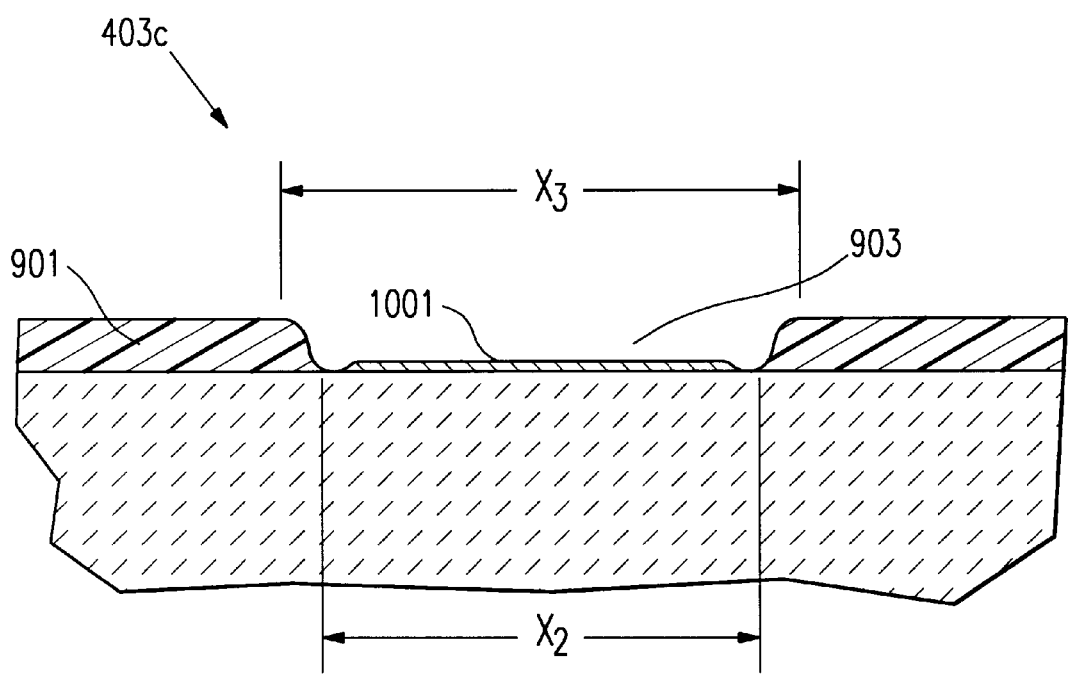
FIG. 11 is a cross-sectional view of one of the hematocrit sensors showing the first layer of encapsulant in accordance with one embodiment of the present invention.

Once the cathode conductor 707 has been dried and fired, a resistor 412 is preferably deposited on the back side of the substrate 405, as shown in FIG. 3. The resistor 412 is coupled in series with the heater 601 in order restrict the current to an appropriate level through the heater during electrical conduction. Next, a first layer of an encapsulant is deposited on the front side of the substrate 405. FIG. 10 is a cross-sectional view of a sensor 403 showing the first layer of encapsulant 901. FIG. 11 is a cross-sectional view of one of the hematocrit sensors 403c showing the first layer of encapsulant 901. It should be noted that FIGS. 10 and 11 are not to scale and that the first layer of encapsulant 901 is preferably very thin (i.e., preferably only a few microns). The encapsulant 901 is deposited essentially over the entire front side of the substrate 405 in order to prepare the surface of the substrate to receive a polymer, as will be discussed in more detail below. In accordance with the preferred embodiment of the present invention, the encapsulant 901 is deposited through a screen using a conventional thick film technique. The screen preferably has a density of 250 wires per inch (with a wire diameter of approximately 0.0016), and an emulsion thickness of 0.0007 inches. The screen masks the encapsulant 901 from forming over the thermistor 409 and metallic layers 704, 706 of each of the sensors. However, in the preferred embodiment, the distal end 703, 703' of the anode 701, 701' and the entire cathode conductor 707 are encapsulated, as shown for example in FIG. 7. A high quality encapsulant is preferably used which will not undergo chemical alteration in the presence of a caustic solution (such as blood or other aqueous solvents). For example, in the preferred embodiment, the encapsulant is part number ESL 4904, available from Electro-Science Laboratories, Inc. However, the thermistor 409 is preferably not encapsulated with the higher quality encapsulant, since such high quality encapsulants typically require firing at high temperatures (850° C., for example in the case of encapsulant used in the preferred embodiment). Such high temperatures will cause the thermistor 409 to deform. Therefore, only after firing the high quality encapsulant can the thermistor be encapsulated. Accordingly, in the preferred embodiment of the present invention, the thermistor 409 is encapsulated with an encapsulant which may be fired at a low temperature.

In the preferred embodiment of the present invention, a second layer of encapsulant 905 is deposited only over the cathode conductor 707 in order to ensure that the cathode conductor is securely isolated. In one embodiment of the present invention, the second layer of encapsulant 905 is applied in two screening procedures in order to provide a total desired thickness for both the first and second layers of encapsulant of approximately 27–47 $\mu M$. While alternative embodiments of the present invention may employ an encapsulant layer which differs in thickness, a thickness in the range of approximately 27–47 $\mu M$ provides satisfactory isolation of the cathode conductor 707. Furthermore, a single layer of encapsulant provides sufficient treatment of the surface of the substrate 405 to allow a polymer to be deposited and bonded to the substrate 405, as further explained below.

After the encapsulant 901, 905 are deposited over the cathode conductor 707, a hole is preferably laser drilled through the encapsulant 901, 905 to expose a portion of the cathode conductor 707, and thus form the cathode 717. The cathode may be laser drilled either before or after firing the encapsulant. The laser targets 417, 418 are used to visually align the laser apparatus in order to drill the hole at the correct location. That is, the lower horizontal edge of the target 417 identifies a line in the horizontal direction. Likewise, the leftmost edge of the laser target 418 identifies a line in the vertical dimension. The cathode is then formed at the intersection of these two lines. Alternatively, the cathode 717 is formed by masking a portion of the cathode conductor 707 in order to prevent the encapsulant 901 from forming over that portion of the cathode conductor 707. In yet another embodiment of the present invention, the cathode 717 may be exposed by a chemical etch. It will be clear to those skilled in the art that numerous other methods may be used to expose a portion of the cathode conductor 707 in order to form a cathode 717.

After applying the first and second encapsulant layers to the front of the substrate 405, a thermistor encapsulant 413 is deposited over the thermistor 409. The thermistor encapsulant 413 can be fired at a relatively lower temperature (such as approximately 595° C.) and thus firing of the thermistor encapsulant 913 does not disturb the geometry of the thermistor 409. In one embodiment of the present invention, the thermistor encapsulant 413 is applied in two screenings in order to achieve a desired thickness and to ensure that no pores are formed in the encapsulant 413. It will be understood by those skilled in the art that the encapsulant over the thermistor 409 should remain relatively thin in order to avoid adding any delay in the sensing of the temperature of the sensor assembly 400. In addition, a resistor encapsulant 415 is deposited over the resistor 412 on the back side of the substrate 405. The resistor encapsulant 415 is preferably the same material as the thermistor encapsulant 413.

After the resistor encapsulant 413 has been deposited on the back side of the substrate 405, a first polymeric layer 1101 is deposited on the front side of the substrate 405. The first polymeric layer (together with the first encapsulation layer 901) forms the lower wall 902 of a plurality of sensor cavities 903 (see FIGS. 10 and 11). The polymer of the preferred embodiment of the present invention is screen printable, absorbs minimal moisture, chemically isolates the membrane chemistries of adjacent cavities, and produces a strong solution bond with the polymeric membrane. The polymer also forms a strong bond with the dielectric layers when exposed at the inside surface of the cavity by an appropriate solvent (such as tetrahydrofuran, xylene, dibutyl ester, and carbitol acetate or any cyclohexanone solvent) in the membrane formation, as will be discussed in further detail below.

The polymer used to form the layer 1101 is preferably a composition of 28.1% acrylic resin, 36.4% carbitol acetate, 34.3% calcined kaolin, 0.2% fumed silica, and 1.0% silane, noted in percentage by weight. The acrylic resin is preferably a low molecular weight polyethylmethacrylate, such as Elvacite, part number 2041, available from DuPont. The calcined kaolin is preferably a silaninized kaolin, such as part number HF900, available from Engelhard. The silane is preferably an epoxy silane, such as trimethoxysilane. Silane bonds to the hydroxyl groups on the glass encapsulant over the substrate, and yet is left with a free functional group to crosslink with the resin's functional group. In accordance with one embodiment of the present invention, the first polymeric layer 1101 is deposited in three screening processes in order to attain the desired thickness (i.e., preferably approximately 0.0020 inches). The first polymeric layer is dried after each screening process. A second polymeric layer 1103 is deposited to form an upper wall 904 of the sensor cavities 903. The first and second polymeric layer 1101, 1103 differ only in the diameter across the cavity at the lower cavity wall 902 and at the upper cavity wall 904 and the number of screening processes that are required to achieve the desired depth. In the case of the second polymeric layer, 10 screening procedures are performed. The second polymeric layer is dried after each screening procedure. In addition, after the last two procedures, the polymer is both screened and cured. In the preferred embodiment of the present invention, the last screening procedure may be omitted if the second polymeric layer has achieved the desired thickness (i.e., preferably 0.0075–0.0105 inches after curing).

The diameter of the cavities are preferably carefully controlled to aid in controlling the deposition of the membranes which are placed over the electrodes of the sensors (i.e., the shape and thickness of the membranes). That is, the sensor cavities enable a droplet of polymeric membrane solution to be captured and formed into a centrosymmetric form over the electrode with sufficient surface contact with the walls of the cavity to assure that the membrane remains physically attached.

Preferably, the sensor cavities 903 for the pH sensor 403e, the electrolyte sensors 403f, 403g, 403h, and the hematocrit sensor 403c, 403d, each have a total depth of approximately $y=0.0075$ inches, a diameter at the upper wall 904 of approximately $x_1=0.070$ inches, and at the lower wall of approximately $x_2=0.06$ inches (see FIG. 10). The diameter $x_3$ of the carbon dioxide sensor cavity 903 is slightly larger than the diameter $x_1$ of the electrolyte sensors 403e–403f and the hematocrit sensor electrodes 403b, 403c. In the preferred embodiment, the diameter $x_3$ is equal to 0.078 inches (see FIG. 11). In accordance with one embodiment of the present invention, the sensor electrodes are spaced apart approximately 0.090 to 0.300 inches from center to center. In accordance with another embodiment, the sensor electrodes are spaced apart from edge to edge by less than half the diameter of the cavity in which the electrode is formed. It should be understood that a membrane of the same thickness may be produced by increasing the diameter of the sensor cavity 903 and increasing the volumetric quantity of the membrane solution that is applied to the sensor in proportion to the increase in the volume of the cavity. Likewise, the same thickness can be maintained by decreasing the diameter of the sensor cavity 903 and proportionally decreasing the volumetric quantity of the membrane solution. It will be clear to those skilled in the art that in an alternative embodiment of the present invention, the sensor cavities may have a shape other than the generally cylindrical shape disclosed above. For example, in accordance with one embodiment of the present invention, the electrodes are formed in an oval shape to reduce the required volume of a sample. However, in the preferred embodiment, the sensor cavities are either cylindrical or generally conical.

Once the sensor cavities 903 have been formed and the polymeric layers dried, the surface of each silver potentiometric electrode is chemically chloridized. The cavity 903 of each ion sensitive sensor is filled with an electrolyte which is appropriate to the particular type of sensor 403. In the preferred embodiment of the present invention, the electrolyte used in the sodium, potassium and calcium electrolyte sensors are ions of inorganic salts that disassociate in solution, such as NaCl, KCl, or $CaCl_2$. In accordance with one embodiment of the present invention, the deposited electrolyte solution is evaporated to a solid form. Alternatively, the electrolyte remains a liquid or a hygroscopic water insoluble gel that acts as a support to immobilize the electrolyte. In accordance with one embodiment of the present invention, such a gel may crosslinked after transfer to the cavity 903. Furthermore, in accordance with one embodiment, the gel undergoes polymerization by a catalyst contained within the solution. In one such embodiment, the gel is polymerized by activating a catalyst with heat or radiation.

The gelled polymeric electrode is preferably one of the following, or a mixture of these: (1) starch, (2) polyvinyl alcohol, (3) polyacrylamide, (4) poly (hydroxy ethyl methacrylate), or (5) polyethylene glycol or polyethylene oxide ether, or another long chained hygroscopic polymer. Hygroscopic polysaccarides or natural gelatin are preferably added to the electrolyte solution.

The electrolyte used in the pH sensor preferably has an acidic pH in the range of about 3–7. In accordance with one embodiment, the electrolyte is an aqueous solution of potassium hydro phosphate ($KH_2PO_4$), preferably has 13.6 grams of potassium hydro phosphate in one liter of deionized water. The electrolyte suppresses the reaction of carbon dioxide and water to minimize the extent to which the carbon dioxide influences the pH of the electrolyte. This favors the pH response for pH measurement and minimizes the response of $CO_2$. The electrolyte for $pCO_2$ sensor is initially alkaline in the range of approximately 7–14. However, in the preferred embodiment of the present invention, the electrolyte is within the range of 8–9 due to the presence of bicarbonate ions. In accordance with the present invention, the electrolyte for the $pCO_2$ sensor is preferably 0.02 moles of sodium bicarbonate in a liter of deionized water. Solutions in either liquid or gel phase may be used. A sensor which includes such an electrolyte is also described in U.S. Pat. No. 5,336,388, assigned to PPG Industries, Inc, which is incorporated in its entirety by this reference. In addition, U.S. Pat. Nos. 5,246,576 and 5,342,498, each assigned to the assignee of the present invention, are hereby incorporated in their entirety by this reference.

The electrolyte of the oxygen sensor 403b provides a low impedance contact across the anode and cathode and establishes a standard chemical potential as is the case in the aforementioned potentiometric sensors. Suitable electrolytes are NaCl and KCl. The electrolyte may be either a fluid or a gel. The preferred use of the electrolyte is in a buffered solution such as one having 0.1 mole potassium hypophosphite ($KH_2PO_3$).

Some of the aforementioned electrolytes including the oxygen sensor are preferably encapsulated by a selectively permeable, hydrophobic membrane that serves to trap the electrolyte against the electrode. Some of these sensors have membranes (except for the oxygen and $pCO_2$ sensors), which can include a polymer, a plasticizer, an ionophore, a charge screening compound (also known as a phase transfer catalyst), and a solvent. The membranes are ion-selective permeable barriers that restrict the free passage of all but the desired ion. The membrane preferably comprises an inert lyophilic polymer dispersed in an organic plasticizer. The membrane is preferably in the range of approximately 5–250 $\mu$m thick.

Water molecules will rapidly diffuse across these membranes. In accordance with one embodiment of the present invention, the inert polymer is polyvinylchloride (PVC).

However, in an alternative embodiment, other ion permeable polymers may be used, such as (1) copolymeric vinyl ethers, (2) porous polytetraflourethelene (PTFE), (3) silicones, (4) cellulose acetate, (5) poly (methlymethacrylate), (6) polystyrene acrylate, (7) methacrylate copolymers, (8) polyimides, (9) polyamides, (10) polyurethanes, (11) polybisphenol-Acarbonate (polysiloxane/poly(bisphenol-Acarbonate)blocked copolymer, (12) poly(vinylidene chloride); and (13) lower alkyl acrylate and methacrylate copolymers and polymers. It will be clear to those skilled in the art that this list is not exhaustive, and that other such ion permeable polymers may be used.

Furthermore, suitable plasticizers include (1) dioctyl adipate, (2) bis(2-ethylhexyl)adipate, (3) di-2-ethlylhexyladipate, (4) dioctyl phthalate, (5) 2-nitrophenyl octyl ether (NPOE), (6) diotcyl sebacate, (7) nitrobenzene, (8) tri(2-ethylhexyl) phosphate, (9) dibutyl sebacate, (10) diphenyl ether, (11) dinonyl phthatlate, (12) dipenyl phthalate, (13) di-2-nitrophenyl ether, (14) glycerol triacetate, (15) tributyl phosphate, (16) dioctyl phenyl phosphate, and similar long chained ethers and hydrocarbons, and combinations thereof. In the preferred embodiment, a combination of bis(2-ethylhexyl)adipate, 2-nitrophenyloctylether or 0-nitrophenyloctylether (NPOE), and nitrobenzene are used as the plasticizer for the pH and $CO_2$ sensor. Dioctyl phthalate is preferably used as the plasticizer in the calcium, potassium and sodium sensor membranes.

The membrane polymers and plasticizers are preferably soluble in organic solvents, such as cyclohexanone, tetrahydofuran, xylene, dibutyl ester, and carbital acetate. In accordance with one embodiment of the present invention, such solvents are removed from the membrane after application over the electrode by vacuum drying at ambient temperatures or low temperatures less than 100° C. The solvent softens the organic layer on the substrate that supports the membrane and encapsulates the internal electrolyte over the electrode while allowing penetration of the membrane by the ion via the complexing agent or ionophore. In accordance with one embodiment of the present invention, after encapsulation, the internal electrolyte is hydrated for a predetermined period prior to use to allow water vapor to permeate the membrane and form an internal electrolyte solution producing a chemically and physically uniform distribution of charge on the electrode.

It will be understood by those skilled in the art that any ionophore or ion exchanger that mediates the interaction of the ion with the environment and which facilitates the translocation of the ion would be suitable for use in the membrane of the present invention. For example, in the present invention the ionophore or ion exchanger may be any of the following: (1) tridodecylamine (TDDA), (2) tri-n-dodecylamine, (3) valinomycin ($K^+$); (4) methyl monesin ($Na^+$), or (5) tridodecylmethyl-ammonium chloride ($Cl^-$). A lipophilic organic anion serving as a balancing specie, such as tetraphenyl borate, is preferably present to provide a membrane with net neutral charge. The membranes of the present invention provide accurate detection and fast response over long periods of use.

The oxygen sensor membrane restricts access of electroactive materials other than oxygen to the electrode surface while allowing free diffusion of oxygen to the electrode surface.

All membrane solutions are dispensed in the sensor cavities using automated fluid dispensing systems. These systems have three main parts: (1) a horizontal x-y-z motorized and programmable table (such as those available from Asymtek of Carlsbad, Calif.); (2) a precision fluid metering pump (such as those available from Fluid Metering, Inc. of Oyster Bay, N.Y.); and (3) a personal computer control unit. All three parts are linked by a digital communication protocol. Software for set-up and dispensing a sequence of liquid microvolumes communicates the x, y, and z positions to the table, and timing of the dispensing pump controller. At each cavity, the metering pump transfers a preset volume of electrolyte or membrane solution through fine diameter tubing from a supply reservoir to a needle or nozzle mounted on the motorized axes of the table and then to the substrate cavity. The fluid may be successfully dispensed with a number of different pumps; pinch tube, rotary positive displacement or diaphragm valves. The drop size is generally no larger than one diameter of the sensor cavity.

After dispensing the aqueous or organic solution, the membrane is formed by drying or curing liquid. Drying removes the solvent components by evaporation. The drying process may be performed by heating or applying a vacuum pressure. Some organic solutions may be cured either thermally or by exposure to ultra-violet radiation.

The combination of the geometry, membrane composition, and aqueous or organic internal electrolyte have been found to yield membranes of minimal thickness, with controlled diffusion paths so that potentiometric sensors may detect a varying concentration of gas. Elimination of in-plane electrical connections to the electrode by use of a subminiature through hole assures better control of the electro-chemical processes. In addition, the use of subminiature through holes improves the flatness of the bonding surface of the polymer coating laminated on the substrate for better bonding and sealing of the flowcell.

Figure 12:
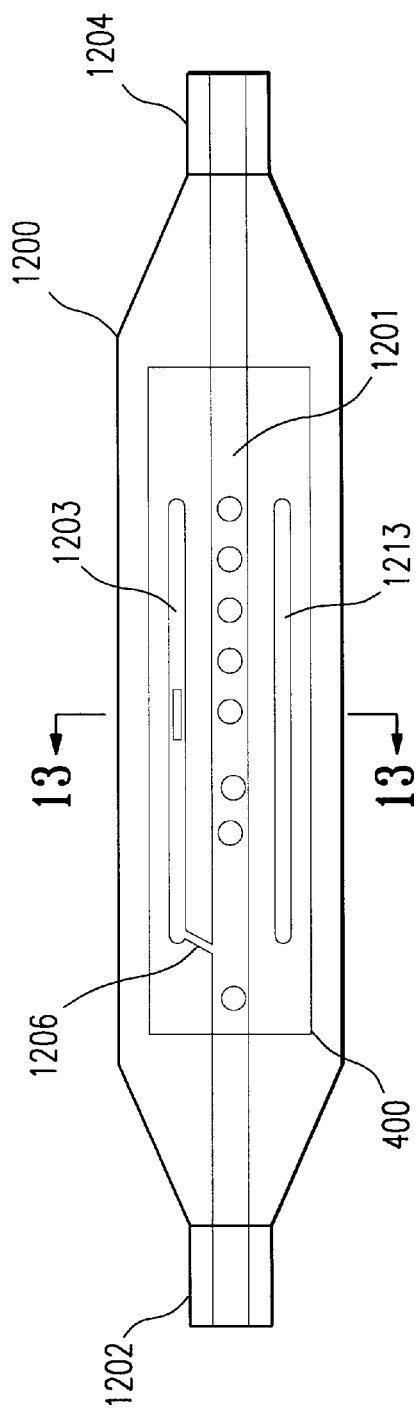
FIG. 12 is a top plan view of the sensor assembly installed within a plastic encasement.
Figure 13:
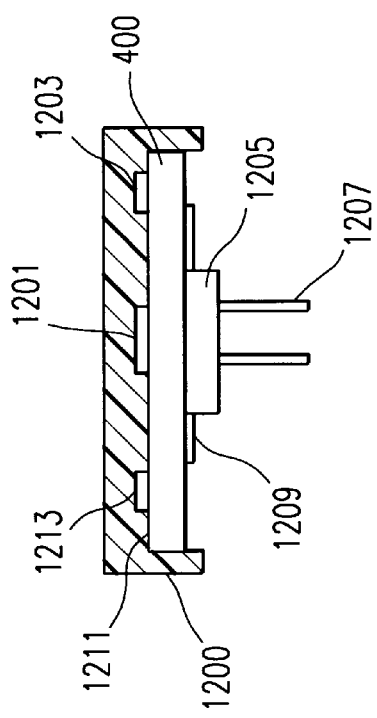
FIG. 13 is a cross-sectional view of the sensor assembly installed in the plastic encasement.

FIG. 12 is a top plan view of the sensor assembly 400 installed within a preferably transparent or translucent plastic encasement 1200. FIG. 13 is a cross-sectional view of the sensor assembly 400 installed in the plastic encasement 1200. In accordance with one embodiment of the present invention, the encasement 1200 is a transparent plastic having an outside dimension of less than 0.5 inches by 2.0 inches by 0.25 inches. After each of the electrodes have been completed, the pads 411 are plated with solder. The solder provides an electrical and mechanical interface between the pads 411 and contacts 1209 of a conventional electrical surface mount connector 1205. The contacts 1209 of the surface mount connector 1205 are soldered to the pads 411 in a conventional manner. In addition, the connector 1205 is preferably secured to the substrate 405 by an adhesive, such as an epoxy glue. Electrically conductive pins 1207 of the conventional connector 1205 permit the sensor assembly 400 to be easily installed and in, and removed from, a blood analyzer (not shown). Use of a conventional surface mount connector 1205 results in a reliable interface to the blood analyzer instrumentation, provides a simple design, low cost construction, a simple test interface, and allows critical connections to be spaced apart to ensure high electrical resistance between each critical connection. Furthermore, the conventional surface mount connector 1205 allows the present invention to be mass produced at low cost, and makes the present invention analogous to familiar semiconductor dual-in-line packages.

The front side of the sensor assembly 400 is enclosed in the plastic encasement 1200 which forms a flowcell 1201 and a reference cell 1203. A lap joint 1211 is preferably formed between the sensor assembly 400 and the encasement 1200. In accordance with the preferred embodiment of the present invention, an adhesive, such as epoxy glue, is used to secure the sensor assembly 400 in the encasement 1200. The encasement 1200 is formed with inlet and output ports 1202, 1204, respectively. The inlet and outlet ports 1202, 1204 allow a sample to be injected into, and discharged from, the flowcell 1201. The adhesive seals the reference cell 1203 and the flowcell 1201 along the lap joint, such that fluid can only enter and exit through the inlet and outlet ports 1202, 1204.

The encasement is preferably formed of a material having low oxygen permeability, low moisture permeability, which is transmissive to ultraviolet radiation, and which is resistant to color change upon exposure to ultraviolet radiation, such as a composition of acrylic, styrene, and butadine. Because even the preferred composition absorbs moisture, the encasement 1200 is preferably formed with a third cell 1213. The third cell 1213 reduces the amount of encasing material which is adjacent to the flowcell 1201. However, it will be clear to those skilled in the art that such a third cell 1213 is not necessary for the proper operation of the present invention. In addition, in one embodiment of the present invention, the amount of encasing material is reduced to a minimum to reduce the absorption of oxygen from a sample which is present in the flowcell 1201.

The flowcell 1201 is formed to ensure that a sample which enters the flowcell comes into contact with each of the sensors 403. Furthermore, the flowcell 1201 is very shallow, thus the volume of the flowcell 1201 is very small (i.e., 0.05 milliliters in the preferred embodiment). A very thin reference channel 1206 (preferably 0.005–0.010 inches in diameter) between the reference cell 1203 to the flowcell 1201 provides ionic contact between the reference medium which resides within the reference cell 1203. The reference medium may be any well known reference electrolyte in solution or gel form. However, in the preferred embodiment, the reference medium is preferably a natural polysaccharide, such as agarose, gelatin, or polyacrylamide. The greater viscosity of the reference medium used in the preferred embodiment retards evaporation of the reference medium, as well as preventing the reference medium from intermingling with the fluids in the flowcell 1201. The reference medium is preferably introduced into the reference cell 1203 after the sensor assembly 400 is installed in the encasement 1200. In accordance with the present invention, a vacuum is created in the flowcell 1201 and the reference cell 1203 by applying a low pressure source to either the inlet or outlet port 1204, 1206. The reference medium is then applied to the other port 1206, 1204. Preferably, the reference medium is heated to approximately 37°–50° C. by the heater 601 or by application of heat through an external heat source to reduce the viscosity of the reference medium, and thus allow the reference medium to completely fill the reference cell 1203. Once the gel has filled the reference cell 1203, any excess reference medium is gently flushed from the flow channel prior to allowing the reference medium to cool. In an alternative embodiment of the present invention, the viscosity of the reference medium may be increased in response to a chemical reaction between the medium and a catalyst which is placed into the reference channel either before or after the reference medium.

It should be noted that when the height of the fluid column over the sensor array has been minimized to conserve sample volume (0.10 inches, for example), measurement is preferably made within 10–15 seconds after the sample has entered the flowcell 1201.

It will be seen from the above description of the present invention, that the sensors are not separable into parts, but rather form a signal modular unit, designed for a predefined life, installed once, and then discarded. Discarding the unit is economically feasible due to the low cost at which such sensor assemblies can be fabricated. The present invention makes it possible to provide a low cost system which is built around standardized electronic assemblies by providing a low cost, mass producible sensor assembly that has highly accurate and reproducible results.

It should be clear to those skilled in the art that the use of subminiature through holes to route electrical signals from the electrodes of the sensors to the opposite side of the substrate allow a chemically selective membrane overlaying the planar electrode to function with the desired sensor reaction mechanism while providing a means for packing a number of sensors into a relatively small area on the surface of the substrate. The use of the subminiature through holes also allows for excellent physical isolation of the sample from the conductors that carry the electrical signals between the sensor electrodes and the instrumentation used to process those signals. This physical isolation results in very high electrical isolation between signals generated by each of the sensors.

Figure 14A:
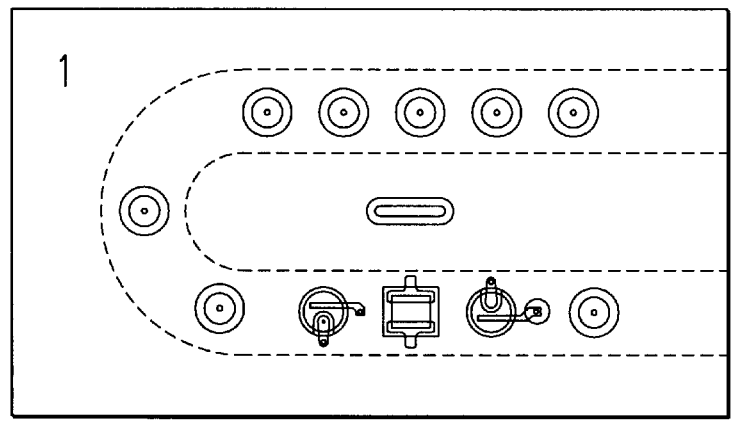
FIGS. 14a–14c illustrate alternative embodiments of the present invention in which the relative positions of the sensors differ from those shown in FIG. 2.
Figure 14B:
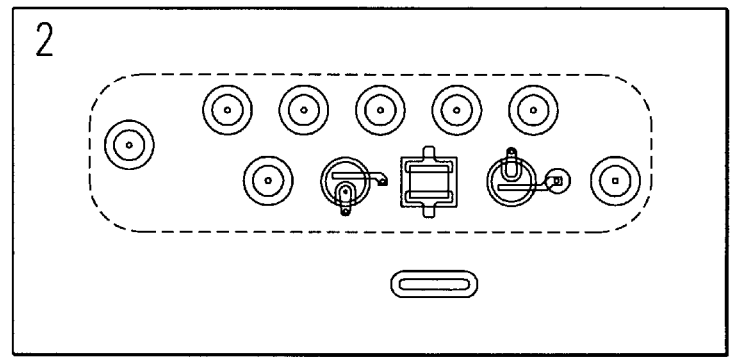
Figure 14C:
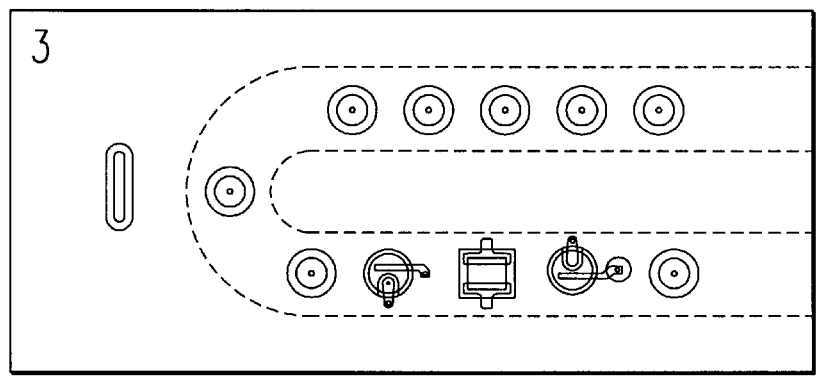

FIGS. 14a–14c illustrate three alternative embodiments of the present invention in which the relative positions of the sensors differ from those shown in FIG. 2. In addition, in accordance with an alternative embodiment illustrated in FIG. 15, the subminiature hole may be drilled at a location other the directly under the sensor electrode. In such an embodiment, an electrical conductor couples the conductive material which fills the subminiature hole with the electrode.

Summary

A number of embodiments of the present invention have been described. Nevertheless, it will be understood that various modifications may be made without departing from the spirit and scope of the invention. For example, while the present invention is described generally as being fabricated using a thick film technique, any other well known layered circuit technique may be used, such as thin film, plating pressurized laminating, and photolithographic etching. Furthermore, substrates for a number of sensor assemblies may be fabricated concurrently on a single section of ceramic material which has preferably been scored to allow for easy separation into individual substrates after deposition of all of the components of the sensor assembly, and prior to installation in an encasement. Accordingly, it is to be understood that the invention is not to be limited by the specific illustrated embodiment, but only by the scope of the appended claims.

What is claimed is:

1. A sensor for use in a fluid analyte analyzer, including:

an electrically insulating substrate defined by at least one planar surface;

a subminiature through hole having a diameter between about 0.002 to about 0.006 inch which traverses the substrate, said subminiature through hole being filled with a conductive material; and a sensor electrode having a diameter between about 0.046 to about 0.078 inch formed on the planar surface over the subminiature through hole, wherein the conductive material disposed within said subminiature through hole is compatible with the material from which the sensor electrode is made and taken from the group consisting of silver, silver/platinum, and alloys of silver and platinum.

2. The sensor of claim 1, wherein the electrical resistance through the insulating substrate is essentially unchanged over periods of at least two months of being subjected to an aqueous electrolyte.

3. The sensor of claim 1, further including a membrane overlying the electrode.

4. The sensor of claim 3, wherein the membrane is approximately 5–250 $\mu$m thick.

5. The sensor of claim 3, wherein the membrane has a larger diameter than the electrode.

6. The sensor of claim 1, further including a polymeric layer deposited over the substrate to form a sensor cavity about the sensor electrode.

7. The sensor of claim 1, further including:

(a) a first polymeric layer deposited over the substrate to form a lower wall defining a sensor cavity about the sensor electrode; and (b) a second polymeric layer deposited over the substrate to form an upper wall further defining the sensor cavity about the sensor electrode.

8. The sensor of claim 7, further including a membrane which at least partially fills the sensor cavity and covers the sensor electrode.

9. The sensor of claim 7, wherein the area of any horizontal cross section of the portion of the sensor cavity defined by the lower wall is less than the area of any horizontal cross section of the portion of the sensor cavity defined by the upper wall.

10. The sensor of claim 7, wherein at least the second polymer includes an adhesive in order to aid in bonding a membrane to the polymer.

11. The sensor of claim 7, wherein at least the second polymer is a composition of 28.1% acrylic resin, 36.4% carbitol acetate, 34.3% calcined kaolin, 0.2% fumed silica, and 1.0% silane.

12. The sensor of claim 11, wherein the acrylic resin is a low molecular weight polyethylmethacrylate.

13. The sensor of claim 11, wherein the calcined kaolin is a silaninized kaolin.

14. The sensor of claim 11, wherein the silane is epoxy silane.

15. The sensor of claim 14, wherein the epoxy silane is trimethoxysilane.

16. A potentiometric sensor for analyzing fluid samples, the sensor including:
   a substrate defined by at least one planar surface;
   a subminiature through hole having a diameter between about 0.002 to about 0.006 inch through the substrate, said subminiature through hole being filled with a conductive material;
   a first metallic sensor electrode having a diameter between about 0.046 to about 0.078 inch formed upon the planar surface of the substrate over the subminiature through hole, wherein the conductive material disposed within said subminiature through holes is compatible with the material from which the sensor electrode is made and taken from the group consisting of silver, silver/platinum, and alloys of silver and platinum;
   a first polymeric layer deposited on the substrate about the metallic sensor electrode defining a lower sensor cavity;
   a second polymeric layer deposited on the first polymeric layer, the second polymeric layer defining an upper sensor cavity, the area of horizontal cross sections of the upper sensor cavity being greater than the area of horizontal cross sections of the lower sensor cavity;
   an electrolyte solution containing ions of inorganic salts that disassociate in solution; and
   a membrane for trapping the electrolyte solution against the electrode.

17. The sensor of claim 16, further including a reference electrode.

18. The sensor of claim 16, further including a second metallic sensor electrode, the second metallic sensor electrode formed over the first metallic sensor electrode and having a smaller average diameter than the first metallic sensor electrode.

19. The sensor of claim 16, wherein at least the second polymer is a composition of 28.1% acrylic resin, 36.4% carbitol acetate, 34.3% calcined kaolin, 0.2% fumed silica, and 1.0% silane.

20. The sensor of claim 19, wherein the acrylic resin is a low molecular weight polyethylmethacrylate.

21. The sensor of claim 19, wherein the calcined koalin is a silaninized kaolin.

22. The sensor of claim 19, wherein the silane is epoxy silane.

23. The sensor of claim 22, wherein the epoxy silane is trimethoxysilane.

24. The sensor of claim 16, wherein the sensor is for sensing sodium and the electrolyte includes at least NaCl.

25. The sensor of claim 16, wherein the sensor is for sensing potassium and the electrolyte includes at least KCl.

26. The sensor of claim 16, wherein the sensor is for sensing calcium and the electrolyte includes at least $CaCl_2$.

27. The sensor of claim 16, wherein the sensor is for sensing pH, and the electrolyte has a pH in the range of approximately 3–7.

28. The sensor of claim 16, wherein the sensor is for sensing pH, and the electrolyte is $KH_2PO_4$.

29. The sensor of claim 16, wherein the sensor is for sensing $pCO_2$, and the electrolyte has a pH in the range of approximately 7–14.

30. The sensor of claim 16, wherein the sensor is for sensing $pCO_2$, and the electrolyte is $NaHCO_3$.

31. The sensor of claim 16, wherein the sensor is for sensing a partial pressure of oxygen, and the electrolyte is NaCl.

32. The sensor of claim 31, wherein the electrolyte is in a buffered solution of 0.1 mole potassium hypophosphite.

33. The sensor of claim 16, wherein the sensor is for sensing partial pressure of oxygen and the electrolyte is KCl.

34. The sensor of claim 33, wherein the electrolyte is in a buffered solution of 0.1 mole potassium hypophosphite.

35. The sensor of claim 16, wherein the membrane includes:
   a. an inert polymer; and
   b. a plasticizer.

36. The sensor of claim 35, wherein the inert polymer is lipophilic.

37. The sensor of claim 35, wherein the inert polymer is polyvinylchoride.

38. The sensor of claim 35, wherein the inert polymer is selected from the group consisting of:
   (h) copolymeric vinyl ether;
   (i) porous polytetraflourethelene;
   (j) silicone;
   (k) cellulose;
   (l) acetate;
   (m) poly(methlymethacrylate);
   (n) polystyrene acrylate;
   (o) methacrylate copolymer;
   (p) polyamide;
   (q) polyamide; and
   (r) polyurethane.

39. The sensor of claim 35, wherein the plasticizer is a long chained ether.

40. The sensor of claim 35, wherein the plasticizer is a long chained hydrocarbon.

41. The sensor of claim 35, wherein the plasticizer is a combination of a long chained hydrocarbon and a long chained ether.

42. The sensor of claim 35, wherein the plasticizer is selected from the group consisting of:
   (a) dioctyl adipate;
   (b) bis-(ethylhexy)adipate;
   (c) di-2-ethylhexyladipate;
   (d) dioctly phthalate;
   (e) o-nitrophenyloctylether; and
   (f) diotcyl sebacate;
   (g) tri(2-ethylhexyl) phosphate;
   (h) dibutyl sebacate;
   (i) diphenyl ether;
   (j) dinonyl phthatlate;
   (k) dipenyl phthalate;
   (l) di-2-nitrophenyl ether;

(m) glycerol triacetate;

(n) tributyl phosphate; and (o) dioctyl phenyl phosphate.

43. The sensor of claim 38, wherein the sensor is for sensing pH and the plasticizer is a combination of bis(2-ethylhexyl)adipate, 2-nitrophenyloctylether, and nitrobenzene.

44. The sensor of claim 35, wherein sensor is for sensing $pCO_2$ and the plasticizer is a combination of bis(2-ethylhexyl)adipate, 2-nitrophenyloctylether, and nitrobenzene.

45. The sensor of claim 35, wherein the sensor is for sensing calcium and the plasticizer is a dioctyl phthalate.

46. The sensor of claim 35, wherein the sensor is for sensing sodium and the plasticizer is a dioctyl phthalate.

47. The sensor of claim 35, wherein the sensor is for sensing potassium and the plasticizer is a dioctyl phthalate.

48. The sensor of claim 35, wherein the membrane further includes:

a. an ionophore;

b. a charge screening compound; and c. a solvent.

49. The sensor of claim 48, wherein the ionophore is TDDA.

50. The sensor of claim 48, wherein the charge screening compound is a borate compound.

51. The sensor of claim 48, wherein the solvent is selected from the group consisting of:

(d) tetrahydrofuran;

(e) xylene;

(f) dibutyl ester;

(g) carbitol acetate; and (h) cyclohexanone.

52. The sensor of claim 48, wherein the solvent is cyclohexanone.

53. The sensor of claim 48, wherein the ionophore is selected from the group consisting of:

(a) TDDA;

(b) tri-n-dodecylamine;

(c) valinomycin;

(d) methyl monesin; and (e) tridodecylmethyl-ammonium chloride.

54. A plurality of sensors formed on a planar surface of a substrate, each sensor being formed in close proximity to at least one other sensor, each sensor including:

a subminiature through hole having a diameter between about 0.002 to about 0.006 inch through the substrate, said subminiature through hole being filled with a conductive material;

a first sensor electrode having a diameter between about 0.046 to about 0.078 inch formed upon the planar surface of the substrate over the subminiature through hole, wherein the conductive material disposed within said subminiature through holes is compatible with the material from which the sensor electrode is made and taken from the group consisting of silver, silver/platinum and alloys of silver and platinum;

a first polymeric layer deposited on the substrate about the metallic sensor electrode defining a lower sensor cavity;

a second polymeric layer deposited on the first polymeric layer, the second polymeric layer defining an upper sensor cavity, the area of horizontal cross sections of the upper sensor cavity being greater than the area of horizontal cross sections of the lower sensor cavity;

an electrolyte solution containing ions of inorganic salts that disassociate in solution; and a selectively permeable membrane for trapping the electrolyte solution against the electrode.

55. The sensors of claim 54, wherein the sensor electrodes are spaced apart by a distance with a range of approximately 0.090 inches to 0.300 inches center to center.

56. The sensors of claim 54, wherein each sensor electrode is formed within a cavity, and the sensor electrodes are spaced apart by a distance less than one half the diameter of one of the sensor cavities measured from edge to edge of the electrodes.

57. The plurality of sensors of claim 54, further including electrical contact pads formed on the substrate on the opposite side from the side of the substrate on which the electrodes are formed, wherein:

a. the conductive material which fills the subminiature through holes is electrically coupled to the electrical contact pads.

58. The sensors of claim 57, wherein the electrical contact pads are aligned to interface with an electrical connection device to allow electrical interconnection between electrodes of the plurality of sensors and circuits which are not on the substrate.

59. The sensors of claim 54, wherein each sensor further includes an electrical conductor in electrical contact with the sensor electrode, and wherein electrical isolation is maintained between the conductors by the insulating properties of the substrate and further by an encapsulant which isolates the conductors from an analyte being exposed to the sensor.

60. The sensors of claim 59, wherein the electrical insulating properties of the encapsulant are maintained in the presence of an aqueous electrolyte.

* * * * *